United States Patent [19]

Mansuri et al.

[11] Patent Number: 5,733,920

[45] Date of Patent: Mar. 31, 1998

[54] INHIBITORS OF CYCLIN DEPENDENT KINASES

[75] Inventors: Muzammil M. Mansuri, Lexington; Krishna K. Murthi, Waltham; Kollol Pal, Needham, all of Mass.

[73] Assignee: Mitotix, Inc., Cambridge, Mass.

[21] Appl. No.: 551,031

[22] Filed: Oct. 31, 1995

[51] Int. Cl.$^6$ ............... A61K 31/44; C07D 405/02
[52] U.S. Cl. ............... 514/337; 514/254; 514/256; 514/274; 514/312; 514/320; 514/324; 514/432; 514/456; 544/238; 544/315; 544/318; 544/408; 546/153; 546/196; 546/283.1; 549/23; 549/401; 549/403
[58] Field of Search .................. 514/254, 256, 514/274, 312, 320, 324, 337, 432, 456; 544/238, 315, 318, 408; 546/153, 196, 283.1; 549/23, 401, 403

[56] References Cited

U.S. PATENT DOCUMENTS

| | | | |
|---|---|---|---|
| 4,603,137 | 7/1986 | Bhat et al. | 514/320 |
| 4,900,727 | 2/1990 | Kattige et al. | 514/212 |
| 5,284,856 | 2/1994 | Naik et al. | 514/320 |

OTHER PUBLICATIONS

Losiewicz, Michael, et al., "Potent Inhibition of CDC2 Kinase Activity By The Flavonoid L86–8275", *Biochemical and Biophysical Research Communications*, vol. 201, No. 2, pp. 589–595 (1994).

Vlahos, Chris J., et al., "A Specific Inhibitor of Phosphatidylinositol 3–Kinase, 2–(4–Morpholinyl)–8–phenyl–4H–1–benzopyran–4–one (LY294002)", *The Journal of Biological Chemistry*, vol. 269, No. 7, pp. 5241–5248 (1994).

Worland, Peter J., et al., "Alteration of the Phosphorylation State of p34$^{cdc2}$ Kinase by the Flavone L86–8275 In Breast Carcinoma Cells", *Biochemical Pharmacology*, vol. 46, No. 10, pp. 1831–1940 (1993).

*Primary Examiner*—C. Warren Ivy
*Assistant Examiner*—Garth M. Dahlen
*Attorney, Agent, or Firm*—Foley, Hoag & Eliot, LLP

[57] ABSTRACT

The invention provides novel inhibitors of cyclin-dependent kinases, in particular inhibitors of the CDK/cyclin complexes such as CDK4/cyclin D1. The novel compounds are analogs of chromones. These compounds can be used for inhibiting excessive or abnormal cell proliferation. Thus, the novel compounds are useful for treating a subject with a disorder associated with excessive cell proliferation, such as cancer.

37 Claims, 2 Drawing Sheets

INHIBITORS OF CYCLIN DEPENDENT KINASES

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra- and extracellular signals. This is achieved by a complex network of proto-oncogenes and tumor-suppressor genes that are components of various signal transduction pathways. Activation of a proto-oncogene(s) and/or a loss of a tumor suppressor gene(s) can lead to the unregulated activity of the cell cycle machinery. This, in turn, will lead to unregulated cell proliferation and to the accumulation of genetic errors which ultimately will result in the development of cancer (Pardee, Science 246:603–608, 1989).

In the eukaryotic cell cycle a key role is played by the cyclin-dependent kinases (CDKs). Cdk complexes are formed via the association of a regulatory cyclin subunit and a catalytic kinase subunit. In mammalian cells, the combination of the kinase subunits (CDC2, CDK2, CDK4, CDK5, CDK6) with a variety of cyclin subunits (cyclin A, B1, B2, D1, D2, D3 and E) results in the assembly of functionally distinct kinase complexes. The coordinated activation of these complexes drives the cells through the cell cycle and ensures the fidelity of the process (Draetta, Trends Biochem. Sci. 15:378–382, 1990; Sherr, Cell 73:1059–1065, 1993). Each step in the cell cycle is regulated by a distinct and specific cyclin-dependent kinase. For example, complexes of Cdk4 and D-type cyclins govern the early GI phase of the cell cycle, while the activity of the CDK2/cyclin E complex is rate limiting for the G1 to S-phase transition. The Cdk2/cyclin A kinase is required for the progression through S-phase and the CDC2/cyclin B complex controls the entry into M-phase (Sherr, Cell 73:1059–1065, 1993).

The CDK complex activity is regulated by mechanisms such as stimulatory or inhibitory phosphorylations as well as the synthesis and degradation of the kinase and cyclin subunit themselves. Recently, a link has been established between the regulation of the activity of cyclin-dependent kinases and cancer by the discovery of a group of CDK inhibitors including $p27^{Kip1}$, $p21^{Waf1/Cip1}$ and $p16^{Ink4/MTS1}$. The activity of $p21^{Waf1/Cip1}$ is regulated transcriptionally by DNA damage through the induction of p53, senescence and quiescence (Harper et al., Cell 75:805–816, 1993). The inhibitory activity of $p27^{Kip1}$ is induced by the negative growth factor TGF-β and by contact inhibition (Polyak et al., Cell 78:66–69, 1994). These proteins, when bound to CDK complexes, inhibit their kinase activity, thereby inhibiting progression through the cell cycle. Although their precise mechanism of action is unknown, it is thought that binding of these inhibitors to the CDK/cyclin complex prevents its activation. Alternatively, these inhibitors may interfere with the interaction of the enzyme with its substrates or its cofactors.

While $p21^{Waf1/Cip1}$ and $p27^{Kip1}$ inhibit all the CDK/cyclin complexes tested, $p16^{Ink4/MTS1}$ blocks exclusively the activity of the CDK4/cyclin D complexes in the early G1 phase (Serrano et al., Nature 366:704–707, 1993), by either preventing the interaction of Cdk4 and Cyclin D1, or indirectly preventing catalysis. As mentioned above, the $p21^{Waf1/Cip1}$ is positively regulated by the tumor suppressor p53 which is mutated in approx. 50% of all human cancers. $p21^{Waf1/Cip1}$ may mediate the tumor suppressor activity of p53 at the level of cyclin-dependent kinase activity. $p16^{Ink4/MTS1}$ is the product of a tumor suppressor gene localized to the 9p21 locus, which is frequently mutated in human cancer cells.

Of all the various kinases, the CDK4/cyclin D complexes are known to play an important role in regulating cell cycle progression in early G1. These complexes function as integrators of various growth factor-induced extracellular signals and as a link between the different signal transduction pathways and other cyclin-dependent kinases. The expression of the cyclin D1 positive regulatory subunit, is deregulated by gene translocations, retroviral insertions and amplifications in parathyroid adenomas, lymphomas, esophageal and breast carcinomas. The targeted overexpression of cyclin D1 in the mammary epithelium of transgenic mice induces mammary adenomas and adenocarcinomas. This confirms that cyclin D1, when overexpressed, acts as an oncogene (Wang et al., Nature 369:669–671, 1994). These data supports the idea that the lack of functional $p16^{Ink4/MTS1}$ or the overexpression of cyclin D1 leads to the deregulation of CDK4/cyclin D1 kinase activity and thereby contribute to uncontrolled cell proliferation.

The prominent role of CDK/cyclin kinase complexes, in particular, CDK4/cyclin D kinase complexes, in the induction of cell proliferation and their deregulation in tumors, makes them ideal targets for developing highly specific anti-proliferative agents.

SUMMARY OF THE INVENTION

The present invention provides inhibitors for the class of enzymes which include the catalytic subunits referred to in the art as "cyclin dependent kinases", or CDKs, such as CDC2, CDK2, CDK3, CDK4, CDK5, CDK6 or CDK7, and regulatory subunits referred to in the art as "cyclins", e.g., cyclin A, B, C, D1, D2, D3, D4, E, F and G. The kinase activities associated with cyclin/CDK complexes are involved in, for example, progression through the cell cycle and are accordingly relevant to controlling proliferation, differentiation and/or apoptosis.

In one aspect of the invention, there is provided a novel class of chromone derivatives which are useful as kinase inhibitors, particularly as inhibitors of CDK complexes. The subject CDK inhibitors can be represented by the general formula:

Formula I

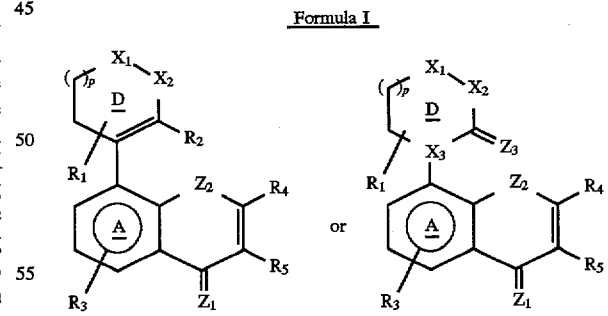

wherein, $Z_1$ and $Z_3$ each can independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

p is 0, 1, or 2;

$R_1$ and $R_3$ represents one or more substitutions to the D ring and the benzene A ring, respectively; and $R_1$, $R_2$, $R_3$, $R_4$, and $R_5$ each can independently represent hydrogen, as valence and stability permit a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an amide, a cyano, a nitro, an azido, a sulfate, a sulfonate, a sulfonamide, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, $R_8$ represents a substituted or unsubstituted aryl, an aralkyl, a cycloalkyl, a cycloalkenyl, or a heterocycle; and n and m are independently for each occurrence zero or an integer in the range of 1 to 6.

In preferred embodiments, each occurrence of $R_3$ independently represents a hydroxyl, a hydroxyl-substituted lower alkyl, an alkoxyl, $-O-C(O)-R'_{12}$ or a lower alkyl substituted with $-O-C(O)-R'_{12}$, wherein, $R'_{12}$ represents a hydrogen, an alkyl, an alkenyl or $-(CH_2)_m-R_8$, where m and $R_8$ are as defined above. Moreover, in certain embodiments, each occurrence of $R_3$ independently represent a hydroxyl group or a group hydrolyzable thereto. By hydrolyzable, it is meant that conversion to a free hydroxyl occurs spontaneously in solution, or can be enzymatically converted by, for example, an esterase, an amidase or other hydrolytic enzyme.

However, most preferred embodiments comprise $R_3$ as a hydroxyl group; and/or $Z_1$, $Z_2$, and $Z_3$ as O; and/or $X_1$ as N and $X_2$ as C. Likewise, preferred CDK inhibitors are those in which $R_4$ represents a substituted or unsubstituted ring selected from a group consisting of benzene, pyrrole, furan, thiophene, imidazole, oxazole, thiazole, triazole, pyrazole, pyridine, pyrazine, pyridazine and pyrimidine (including any isomer of which a heterocyclic ring structure may admit).

For example, certain of the preferred CDK inhibitors can be represented by the general formula:

Formula II

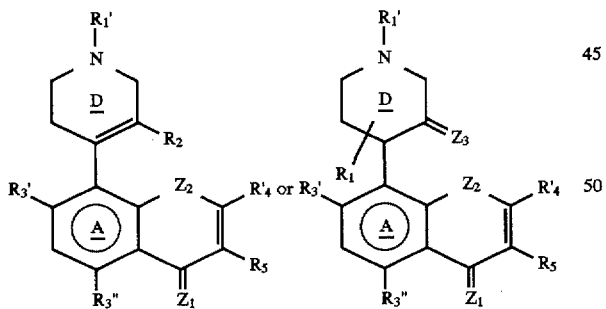

wherein $Z_1$ and $Z_3$ each independently represent O or S;

$Z_2$ represents N, S or O;

$R'_4$ represents an aromatic ring selected from a group consisting of benzene, pyrrole, furan, thiophene, imidazole, oxazole, thiazole, triazole, pyrazole, pyridine, pyrazine, pyridazine and pyrimidine, the aromatic ring being unsubstituted or alternatively substituted at one or more ring positions with halogens, alkyls, alkenyls, alkynyls, hydroxyl, amino, nitro, thiol amines, imines, amides, phosphonates, phosphines, a carbonyl (such as a carboxyl, an ester, a formate, or a ketone), a thiocarbonyl (such as a thioester, a thioacetate, or a thioformate), sulfonyls, ketones, aldehydes, esters, or $-(CH_2)_m-R_8$, $-CF_3$, $-CN$;

$R_1$ represents one or more substitutions to the $\underline{D}$ ring and the benzene $\underline{A}$ ring, respectively; and $R_1$, $R_2$, $R_3'$, $R_3''$, and $R_5$ each independently represent hydrogen, a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an amide, a cyano, a nitro, an azido, a sulfate, a sulfonate, a sulfonamide, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, $R_{1'}$ represents hydrogen, an alkyl, an aralkyl, an aryl, a cycloalkyl, $-C(O)$-lower alkyl, $-C(O)$-lower alkenyl, or $-C(O)-(CH_2)_m-R_8$;

$R_8$ represents a substituted or unsubstituted aryl, a cycloalkyl, a cycloalkenyl, or a heterocycle; and n and m are independently for each occurrence zero or an integer in the range of 1 to 6.

As above for $R_3$, in preferred embodiments $R'_3$ and $R''_3$ each independently represent a hydroxyl, a hydroxyl-substituted lower alkyl, an alkoxyl, $-(CH_2)_m-C(O)-R_{12}$ or $-O-C(O)-R'_{12}$, wherein, $R_{12}$ represents a hydrogen, an alkyl, an alkenyl, $-(CH_2)_m-R_8$ or a pharmaceutically acceptable salt, $R'_{12}$ represents a hydrogen, an alkyl, an alkenyl or $-(CH_2)_m-R_8$, where m and $R_8$ are as defined above. Moreover, in certain preferred embodiments, each of $R'_3$ and $R''_3$ independently represent a hydroxyl group or a group hydrolyzable thereto.

Of these compounds, one class of specifically contemplated CDK inhibitors are those in which the aromatic ring of $R'_4$ is a benzene ring, preferably one which is substituted at one or more ring positions with a halogen. Also, CDK inhibitors are preferred in which $R_3'$ and $R_3''$ are hydroxyl groups or hydrolyzable to hydroxyl groups (as $R_3$ above).

In a most preferred embodiment, the subject CDK inhibitor is a compound represented by the general formula:

Formula III

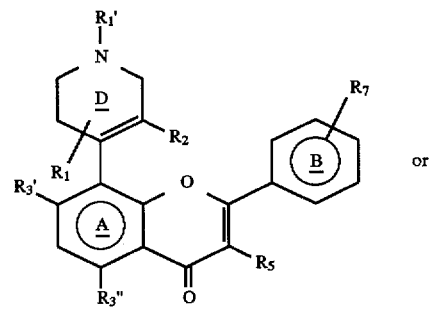

or

-continued
Formula III

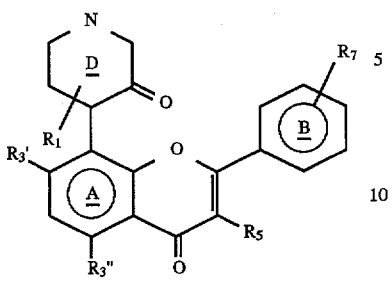

wherein,
R₇ represents one or more substitutions of the benzene ring B;
R₁, R₂, R₃', R₃", R₅, and R₇ each independently represent hydrogen, a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an amide, a cyano, a nitro, an azido, a sulfate, a sulfonate, a sulfonamide, —(CH₂)ₘ—R₈, —(CH₂)ₘ—OH, —(CH₂)ₘ—O-lower alkyl, —(CH₂)ₘ—O-lower alkenyl, —(CH₂)ₙ—O—(CH₂)ₘ—R₈, —(CH₂)ₘ—SH, —(CH₂)ₘ—S-lower alkyl, —(CH₂)ₘ—S-lower alkenyl, —(CH₂)ₙ—S—(CH₂)ₘ—R₈, R₁' represents hydrogen, an alkyl, an aralkyl, an aryl, a cycloalkyl, —C(O)-lower alkyl, —C(O)-lower alkenyl, or —C(O)—(CH₂)ₘ—R₈;

R₈ represents a substituted or unsubstituted aryl, a cycloalkyl, a cycloalkenyl, or a heterocycle; and n and m are independently for each occurrence zero or an integer in the range of 1 to 6.

Preferably, R₁, R₂ and/or R₅ represent hydrogen; R₇ represents a halogen, especially chlorine; and R₃' and R₃" each independently represent hydroxyl groups or groups hydrolyzable thereto as described above.

In preferred embodiments, the subject compounds are inhibitors of the kinase activity of CDK/cyclin complexes, such as CDK/cyclin complexes which are active in G₀ or early G₁ stage of the cell cycle, e.g., CDK4 or CDK6 complexes, e.g., the CDK4/cyclin D1 complex. In other embodiments, the present invention provides compounds which are inhibitors of mammalian CDK/cyclin complexes, as well as inhibitors of insect CDK and of fungal CDK complexes.

As described in more detail below, the present invention further contemplates pharmaceutical preparations comprising a pharmaceutically acceptable carrier and a CDK inhibitor of the present invention in an amount adequate to inhibit proliferation of a eukaryotic cell, e.g., a mammalian cell, an insect cell, a plant cell, and/or a fungal cell. Such preparations can be used to inhibit proliferation of a eukaryotic cell, and/or prevent dedifferentiation of such cells. Accordingly, the subject inhibitors can be used in the treatment of proliferative disorders in mammals, especially humans, marked by unwanted proliferation of endogenous tissue.

Furthermore, the subject inhibitors can be used to prevent or treat mycotic infections, e.g., by inhibiting proliferation of such human pathogens as *Candida albicans, Candida stellatoidea, Candida tropicalis, Candida parapsilosis, Candida krusei, Candida pseudotropicalis, Candida quillermondii, Candida rugosa, Aspergillus fumigatus, Aspergillus flavus, Aspergillus niger, Aspergillus nidulans, Aspergillus terreus, Rhizopus arrhizus, Rhizopus oryzae, Absidia corymbifera, Absidia ramosa,* and *Mucor pusillus.*

When selected for anti-mycotic uses, the formulations of the subject inhibitors can be provided with those inhibitors which inhibit a cyclin dependent kinase complex of the human pathogen with an IC₅₀ at least order of magnitude less than an IC₅₀ for inhibition of a human cyclin dependent kinase complex, though more preferably at least two or three orders of magnitude less.

BRIEF DESCRIPTION OF THE DRAWINGS OF THE INVENTION

DETAILED DESCRIPTION OF THE INVENTION

Figure 1:
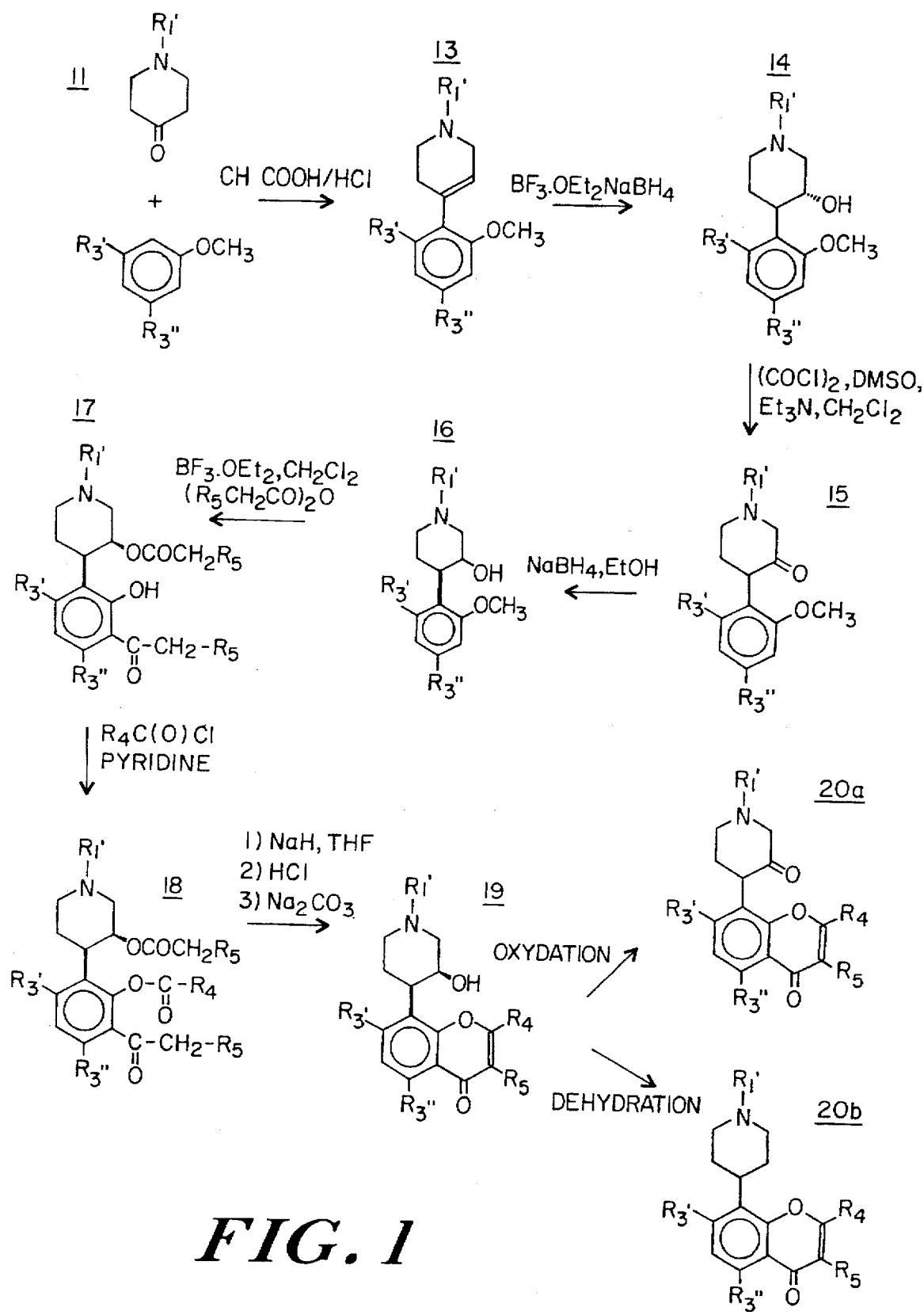
FIG. 1 represents a general synthesis scheme for preparing exemplary compounds of the invention.

The invention pertains to novel inhibitors of cyclin-dependent kinases (CDKs), particularly CDK/cyclin complexes. More specifically, the inhibitors of the invention are analogs of chromones.

The invention is based at least in part on the observation that specific analogs of benzopyranones (and analogs thereof) are capable of inhibiting the kinase activity of complexes including cyclin-dependent kinases (CDKs), such as CDK4 and CDC2. Furthermore, certain of these benzopyranone analogs are shown to be specific for the kinase activity of a CDK/cyclin, being significantly weaker inhibitors of other kinases, such as Epidermal Growth Factor Receptor (EGFR) and Protein Kinase C (PKC).

As described herein, the cyclin-dependent kinase inhibitors of the invention are capable of inhibiting kinases involved in cell-cycle progression and consequently are useful for modulation of cell-cycle progression, and therefore ultimately of cell growth and differentiation. Such compounds can, for example, be used for treating subjects having a disorder associated with excessive cell proliferation, such as in the treatment of various cancers, psoriasis, immunological disorders involving unwanted proliferation of leukocytes, in the treatment of restenosis and other proliferative smooth muscle disorders, and the like. Moreover, as described below, the subject CDK inhibitors can be used to prevent dedifferentiation of post-mitotic tissue and/or cells.

I. Definitions

For convenience, certain terms employed in the specification, examples, and appended claims are collected here.

The terms "chromone" and "benzopyranone" are intended to mean a compound having the following general chemical structure:

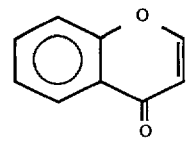

An analog of a chromone is intended to mean any derivative of a chromone, in particular derivatives in which the oxygens are replaced by other atoms and derivatives in which additional chemical groups are attached to any of the carbon atoms of the molecule. For example, the present invention specifically contemplates the use of substituted benzothiopyranones, e.g., Z₁=sulfur in Formula I infra, as well as benzopyridones, e.g., Z₂=nitrogen in Formula I infra.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl, alkoxyl, ester, ether, phosphoryl, cyano, amino, amido, imino, sulfhydryl, alkylthio, thioester, sulfonyl, nitro, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, iminos, amidos, phosphoryls (including phosphonates and phosphinates), sulfonyls (including sulfates, sulfonates and sulfonamides), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, cyano (—CN), and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

As used herein, the term "nitro" means —$NO_2$; the term "halogen" designates —F, —Cl, —Br or —I; the term "sulfhydryl" means —SH; the term "hydroxyl" means —OH; the term "sulfonyl" means —$SO_2$—; and the term "organometallic" refers to a metal atom (such as mercury, zinc, lead, magnesium or lithium) or a metalloid (such as silicon, arsenic or selenium) that is bonded directly to a carbon atom, such as a diphenylmethylsilyl group.

The term "amino" is art recognized and refers to both unsubstituted and substituted amines, e.g., a moiety that can be represented by the general formula:

wherein $R_8$ and $R_9$ each independently represent a hydrogen, an alkyl, an alkenyl, —$(CH_2)_m$—$R_7$, —$C(=O)$-alkyl, —$C(=O)$-alkenyl, —$C(=O)$-alkynyl, —$C(=O)$—$(CH_2)_m$—$R_7$, or $R_9$ and $R_8$ taken together with the N atom to which they are attached complete a heterocycle having from 4 to 8 atoms in the ring structure; $R_7$ represents an aryl, a cycloalkyl, a cycloalkenyl, a heterocyclyl or a polycyclyl; and m is zero or an integer in the range of 1 to 8. In preferred embodiments, only one of $R_8$ or $R_9$ can be a carbonyl, e.g., $R_8$, $R_9$ and the nitrogen together do not form an imide. In even more preferred embodiments, $R_8$ and $R_9$ each independently represent a hydrogen, an alkyl, an alkenyl, or —$(CH_2)_m$—$R_7$. Thus, the term "alkylamine" as used herein means an amine group, as defined above, having a substituted or unsubstituted alkyl attached thereto, i.e., at least one of $R_8$ and $R_9$ is an alkyl group.

The term "amide" is art recognized as an amino-substituted carbonyl and includes a moiety that can be represented by the general formula:

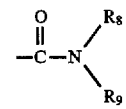

wherein $R_8$ and $R_9$ are as defined above. Again, as will be appreciated in the art, preferred embodiments of the amide will not include imides which may be unstable.

The term "imine" is art recognized and includes a moiety that can be represented by the general formula:

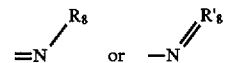

wherein $R_8$ is as described above, and $R'_8$ is selected from the group alkyls, alkenyls, and —$CH_2$—$(CH_2)_m$—$R_7$, wherein $R_7$ and m are as described above. In preferred embodiments, $R_8$ and $R'_8$ are selected from the group alkyls, alkenyls, and —$CH_2$—$(CH_2)_m$—$R_7$.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_7$, wherein m and $R_7$ are defined above. Representative alkylthio groups include methylthio, ethyl thio, and the like.

The term "carbonyl" is art recognized and includes such moieties as can be represented by the general formula:

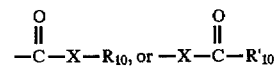

wherein X is a bond or represents an oxygen or a sulfur, and $R_{10}$ represents a hydrogen, an alkyl, an alkenyl, —$(CH_2)_m$—$R_7$ or a pharmaceutically acceptable salt, $R'_{10}$ represents a hydrogen, an alkyl, an alkenyl or —$(CH_2)_m$—$R_7$, where m and $R_7$ are as defined above. Where X is an oxygen and $R_{10}$ or $R'_{10}$ is not hydrogen, the formula represents an "ester". Where X is an oxygen, and $R_{10}$ is hydrogen, the formula represents a "carboxylic acid". Where X is an oxygen, and $R'_{10}$ is hydrogen, the formula represents a "formate". In general, where the oxygen atom of the above formula is replaced by sulfur, the formula represents a "thiocarbonyl" group. Where X is a sulfur and $R_{10}$ or $R'_{10}$ is not hydrogen, the formula represents a "thioester." Where X is a sulfur and $R_{10}$ is hydrogen, the formula represents a "thioacetate." Where X is a sulfur and $R'_{10}$ is hydrogen, the formula represents a "thioformate." On the other hand, where X is a bond, and $R_{10}$ is not hydrogen, the above formula represents a "ketone" group. Where X is a bond, and R$_{10}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_7$, where m and R$_7$ are described above.

The term "sulfonate", as used herein, refers to a moiety that can be represented by the general formula::

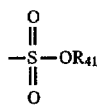

in which R$_{41}$ is an electron pair, hydrogen, alkyl or aryl.

The term "sulfate", as used herein, refers to a moiety that can be represented by the general formula:

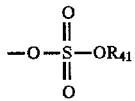

in which R$_{41}$ is as defined above; or R$_{41}$, taken together with the sulfonyl group and the oxygen atoms to which they are attached, may form a ring structure having from 5 to 10 members.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls, alkenoxyls, and alkynoxyls.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, sulfonamido, ketone, aldehyde, ester, a heterocyclyl, an aromatic or heteroaromatic moiety, —CF$_3$, —CN, or the like.

The terms "heterocyclyl" or "heterocyclic group" refer to 4- to 10-membered ring structures, more preferably 4- to 7-membered rings, which ring structures include one to four heteroatoms. Heterocyclyl groups include pyrrolidine, oxolane, thiolane, imidazole, oxazole, piperidine, piperazine, morpholine, lactones, lactams such as azetidinones and pyrrolidinones and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through nonadjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphine, carbonyl, carboxyl, silyl, ether, alkylthio, sulfonyl, ketone, aldehyde, ester, a heterocyclyl, an aromatic or heteroaromatic moiety, —CF$_3$, —CN, or the like.

A "bridging substituent" refers to a substitution at two (or more) sites on a ring by the same (as opposed to identical) substituent so as to form a covalent bridge between the substitution sites. For example, a bridging substituent may be represented by the general formula or —R$_{16}$—R$_{17}$—R$_{18}$—, wherein R$_{16}$ and R$_{18}$ each independently are a bond or represent an alkyl, an alkenyl, or an alkynyl, preferably C$_1$ to C$_{10}$, and R$_{17}$ is a bond, amino, amido, phosphoryl, carbonyl, silyl, oxygen, a sulfonyl, sulfur, or an ester.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorus.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The term "unwanted proliferation" refers to proliferation of cells which is undesired, be it due to transformation of the cells, e.g., neoplastic or hyperplastic, for purposes of wound healing, treatment of restenosis and other unwanted smooth muscle proliferation, cosmetic applications, etc. Likewise, the term "unwanted differentiation" refers to an undesirable change in the differentiation of a cell, such as unwanted dedifferentiation.

II. Compounds of the Invention

In general, the CDK inhibitors of the present invention are derived from 2, 3, 5, 7, 8-substituted chromones, or analogs thereof. In particular, the benzopyranone-derived structures are substituted in the 8 position with a substituted or unsubstituted cycloalkyl or heterocycle, termed "D ring" herein. Preferred CDK inhibitors of the present invention include compounds of the general formula (Formula I):

Formula I

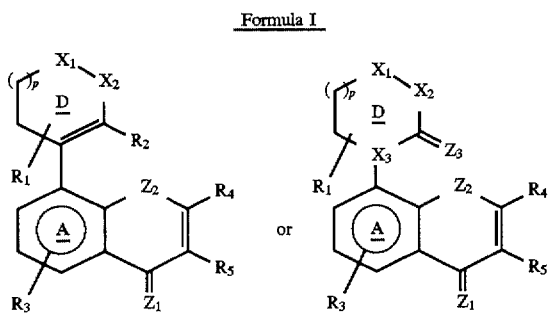

wherein, $Z_1$ and $Z_3$ each independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

p is 0, 1, or 2; and $R_1$ and $R_3$ each independently represent one or more substitutions, as valence permits, to the D ring and the A ring, respectively.

$R_1$, $R_2$, $R_3$, $R_4$, and $R_5$ each independently represent hydrogen, a halogen, a lower alkyl, a lower alkenyl, a lower alkynyl, carbonyl (such as a carboxyl, an ester, a formate, or a ketone), a thiocarbonyl (such as a thioester, a thioacetate, or a thioformate), an amino, an amide, a cyano, a nitro, an azido, a sulfate, a sulfonate, a sulfonamide, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, $R_8$ represents a substituted or unsubstituted aryl, an aralkyl, a cycloalkyl, a cycloalkenyl, or a heterocycle; and n and m are independently for each occurrence zero or an integer in the range of 1 to 6.

As used herein, the definition of each expression, e.g. lower alkyl, m, n, p, etc., when it occurs more than once in any structure, is intended to be independent of its definition elsewhere in the same structure.

In an exemplary embodiment, the subject CDK inhibitors have a chemical structure corresponding to formula I, wherein the D ring is a 6 membered ring, e.g., p=1. For example, derivatives of a piperidyl D ring are specifically contemplated. Moreover, as described in the appended examples, comparison of the inhibitory activity of various subject compounds against CDK4 indicated that the 5,7-hydroxyl substituted benzopyranone derivatives were most potent. Accordingly, in preferred embodiments, at least one of $R_3$ substitutions is hydroxyl or hydroxyl-substituted alkyl, or as a group hydrolyzable to a free hydroxyl, e.g., such as an ester.

In other exemplary embodiments of the invention, the subject CDK inhibitors are represented by formula I, wherein $R_4$ represents a substituted or unsubstituted ring selected from a group consisting of benzene, pyrrole, furan, thiophene, imidazole, oxazole, thiazole, triazole, pyrazole, pyridine, pyrazine, pyridazine and pyrimidine.

Accordingly, in a preferred embodiment, cyclin-dependent kinase inhibitors within the scope of the invention include compounds of the general structure (Formula II):

Formula II

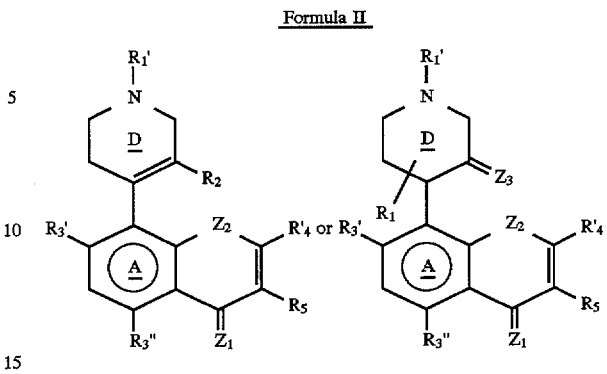

wherein $R'_4$ represents an aromatic ring selected from a group consisting of benzene, pyrrole, furan, thiophene, imidazole, oxazole, thiazole, triazole, pyrazole, pyridine, pyrazine, pyridazine and pyrimidine, the aromatic ring being unsubstituted or alternatively substituted at one or more ring positions with halogens, alkyls, alkenyls, alkynyls, hydroxyl, amino, nitro, thiol amines, imines, amides, phosphonates, phosphines, carbonyls, carboxyls, ethers, thioethers, sulfonyls, ketones, aldehydes, esters, or $-(CH_2)_m-R_8$, $-CF_3$, $-CN$; $R_1'$ represents hydrogen, an alkyl, an aralkyl, an aryl, a cycloalkyl, $-C(O)$-lower alkyl, $-C(O)$-lower alkenyl, or $-C(O)-(CH_2)_m-R_8$; and $Z_1$, $Z_2$, $Z_3$, $R_1$, $R_2$, and $R_5$, are as described above, and $R_3'$ and $R_3''$ represent any of the groups that $R_3$ can represent. Accordingly, $R_1$ represent one or more substitutions at the 2, 3, or 5 positions of the piperidyl D ring.

In a preferred embodiment, the subject CDK inhibitors have a structure represented in Formula II, wherein $Z_1$, $Z_2$, and $Z_3$ are O, and $R'_4$ is a 6 membered aromatic ring, which can be substituted. Such compounds include those having the general structure (Formula III):

Formula III

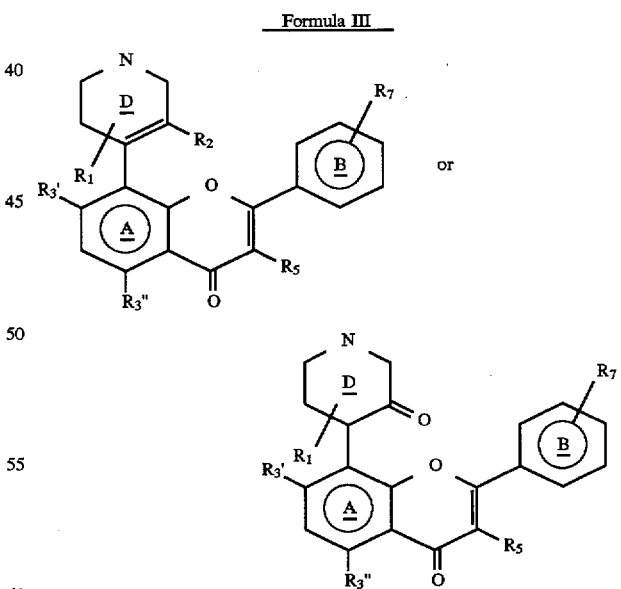

wherein $R_7$ represents one or more substitutions of the benzene ring B;

$R_1$, $R_2$, $R_3'$, $R_3''$, and $R_5$ are as described above and $R_7$ represents hydrogen, a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an amide, a cyano, a nitro, an azido, a sulfate, a sulfonate, a sulfonamide, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$, wherein $R_8$, m and n are as described above.

Preferred inhibitors of cyclin-dependent kinases having a structure corresponding to formula III, are compounds wherein $R_2$ and $R_5$ represent hydrogen. In other embodiments of the invention, preferred inhibitors are those wherein the benzene ring substituted with $R_7$ is a benzene ring substituted with a halogen, more preferably a chlorine, and even more preferably a single chlorine atom in the ortho position.

In more preferred embodiments, each occurrence of $R_3'$ and $R_3''$ independently represents a hydroxyl, a hydroxyl-substituted lower alkyl, an alkoxyl, —O—C(O)—$R'_{12}$ or a lower alkyl substituted with —O—C(O)—$R'_{12}$, wherein, $R'_{12}$ represents a hydrogen, an alkyl, an alkenyl or —$(CH_2)_m$—$R_8$, where m and $R_8$ are as defined above. For the reasons set forth above, $R_3'$ and $R_3''$ are even more preferably hydroxyl groups, or hydrolyzable thereto. By hydrolyzable, it is meant that conversion to a free hydroxyl occurs spontaneously in solution, or can be enzymatically converted by, for example, an esterase, an amidase or other hydrolytic enzyme.

Most preferred inhibitors of cyclin-dependent kinases, which have been shown to efficiently inhibit the activity of the CDK4/cyclin D1 kinase in vitro have the following structure:

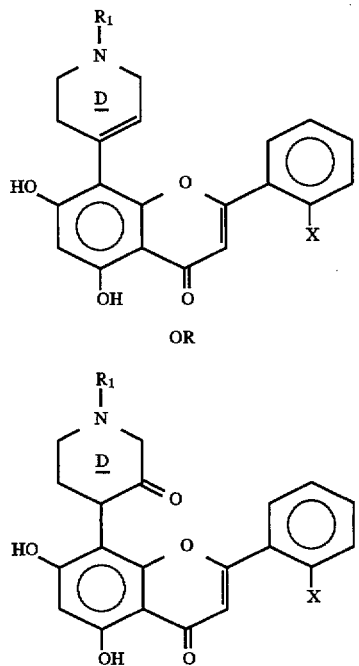

Formula IV wherein $R_1$ and $R_{1'}$ are as described above, and X is a halogen.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

The pharmaceutical acceptable salts of the subject compounds include the conventional nontoxic salts or quaternary ammonium salts of the compounds, e.g., from nontoxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid of Formula I with an appropriate amount of a base such as an alkali or alkaline earth metal hydroxide (e.g. sodium, potassium, lithium, calcium or magnesium) or an organic base such as an amine, piperidine, pyrrolidine, benzylamine and the like, or a quaternary ammonium hydroxide such as tetramethylammonium hydroxide and the like.

Contemplated equivalents of the compounds described in Formula I include compounds which otherwise correspond thereto, and which have the same general properties thereof (e.g. the ability to inhibit the activity of cyclin-dependent kinases), wherein one or more simple variations of substituents are made which do not adversely affect the efficacy of the compound in inhibiting the activity of the cyclin-dependent kinases.

The efficacy of a compound in inhibiting the activity of cyclin-dependent kinases can be determined by several methods well known in the art, such as a kinase assay, as described in the Examples section herein, or as described in Losiewics, M. D., et al. (1994) Biochem. Biophys. Res. Commun. 201, 589. Thus, a complex containing the cyclin-dependent kinase and a cyclin is first isolated either from a recombinant source, or immunoprecipitated from cells synchronized at the stage at which a particular cyclin-dependent kinase is present at high levels in the cell. The immunoprecipitates are then incubated in the presence of radiolabelled ATP and an appropriate substrate with various amounts of the inhibitor. The amount of radioactivity associated with the substrate protein can then be determined by various methods well known in the art. The substrate used for the kinase assay will depend on the specific kinase. Typically, histone H1 or CDK1 S1 is used as a substrate for the CDC2 kinase and the retinoblastoma protein is used as a substrate in a kinase assay for CDK4. The kinases, cyclins, and substrates used in the in vitro kinase assay can be proteins isolated from mammalian cells, or alternatively, they can be proteins produced recombinantly, such as in $E.\ Coli$.

Thus, it is possible to determine the efficacy of the compounds of the invention in inhibiting the activity of various kinases using in vitro kinase assays. Compounds within the scope of the invention include those which inhibit cyclin-dependent kinases in general i.e., the compounds inhibit the kinase activity of most cyclin-dependent kinases. Preferred compounds of the invention include those which inhibit more specifically certain of the CDKs, e.g., the compound selectively inhibits one or two species of cyclin-dependent kinase, such as CDK4/CDK6 or CDC2. Furthermore, other preferred cyclin-dependent kinases of the invention include inhibitors which do not substantially affect the activity of other types of kinases, such as receptor kinases, e.g., Epidermal Growth Factor Receptor (EGFR) or Protein Kinase C (PKC). For example, preferred CDK inhibitors of the present invention have $IC_{50}$'s for CDK inhibition which are at least one order of magnitude smaller than for EGFR or PKC, and more preferably at least two or three orders of magnitude smaller.

III. Synthesis of the Subject CDK Inhibitors

The subject CDK inhibitors of the invention are derivatives of chromones, which can be synthesized according to the following methods.

FIG. 1 represents a general synthesis scheme for preparing compounds having a general Formula V:

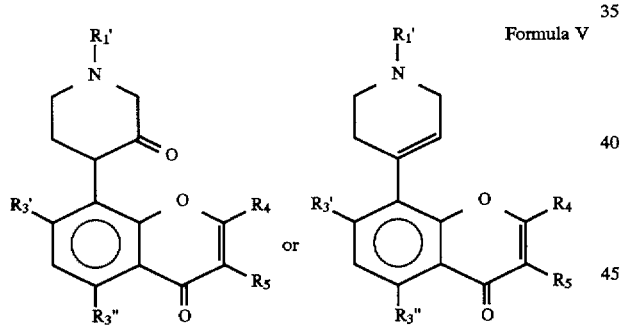

wherein $R_3'$, and $R_3''$ represent a chemical group selected from the chemical groups represented by $R_3$, described above, and $R_1'$, $R_4$ and $R_5$ are as described above.

According to the synthesis scheme, compounds of Formula V are prepared by first reacting an N-substituted piperidinone (compound 11) with a hydroxymethylbenzene derivative (compound 12) to obtain compound 13. Most reagents corresponding to compounds 11 and 12 are commercially available. Compounds 11 and 12 can also be synthesized according to methods known in the art from commercially available reagents.

Numerous modifications of the synthesis scheme represented in FIG. 1 for obtaining compounds 20a and 20b are within the skill in the art. For example, compound 12 can be replaced by a different derivative, e.g., wherein, for example, the methyl group is substituted for another alkyl or derivative thereof.

The general synthesis scheme of FIG. 1 can also be modified by replacing the reactions from compound 17 to compound 19 with the following reactions:

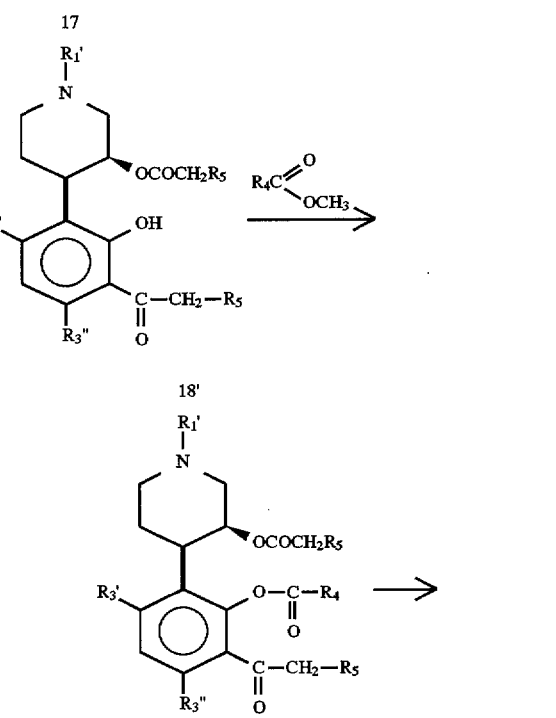

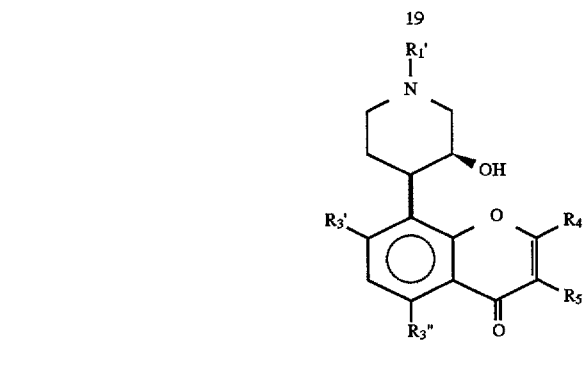

The reagent $R_4C(O)OCH_3$ can be replaced by other acylating reagents, including esters, anhydrides, acid halides, and the like. Examples of these reactions are disclosed, for example, in U.S. Pat. No. 4,900,727. The subject CDK inhibitors of the invention can then be obtained from compound 19 according to the reactions represented in FIG. 1.

Another modification of the general synthesis scheme represented in FIG. 1 includes preparing compound 13 by the following reaction:

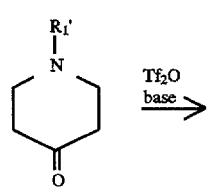

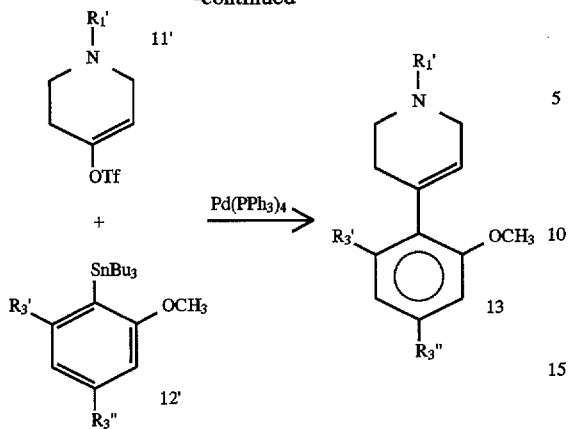

The above depicted reaction for synthesizing compound 13 from compounds 11' and 12' (Stille reaction) is further described in J. Am. Chem. Soc. (1987) 109, 5478 and in the published PCT Application Number PCT/U.S.94/07780. Other compounds 11' that can be used in the Stille reaction are those in which the OTf (triflate) group is replaced by a bromide or an iodine atom. The Stille reaction is a preferred method for preparing compound 13 when the atom of groups $R_3'$ and $R_3''$ linking the R3' and R3" groups to the benzene ring is a carbon atom.

Compound 13 of the general synthesis scheme depicted in FIG. 1 can also synthesized according to the Suzuki reaction, wherein compound 11" of the Stille reaction is reacted with a compound 12" having the general structure (see Miller et al. (1991) Tet Lett 32:2229):

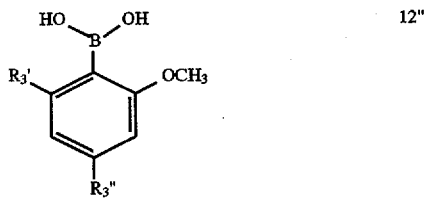

The general synthesis scheme represented in FIG. 1 can also be used for preparing CDK inhibitors having a structure that differs from compounds 20a and 20b of FIG. 1. Examples of such reactions are set forth below.

A subject CDK inhibitor having the general formula VI:

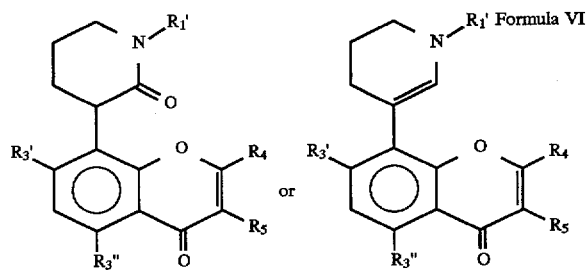

corresponding to compounds of general Formula I, wherein $X_1$ is C and $X_2$ is N, can be synthesized according to the synthesis scheme represented in FIG. 1, using a compound 11''' which has the general formula:

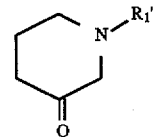

An illustrative embodiment of the synthesis of a CDK inhibitor having the general Formula VI is described in examples 1,3, and 7–12 herein.

The general synthesis scheme represented in FIG. 1 can also be used for preparing compounds wherein the A ring contains an additional substitution, such that all ring positions are substituted. Such a compound could be prepared using a reagent 12''' having the general formula:

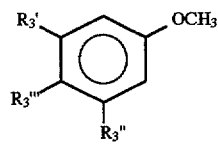

Subject CDK inhibitors having a structure corresponding to general Formula I, wherein the D ring is a 5 or 7 membered ring can also be synthesized according to the general synthesis scheme of FIG. 1, wherein compound 11 is replaced with a compound provided in the form of:

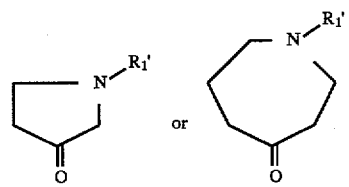

Furthermore, the same synthesis scheme can be used with a compound having a substituted 5-, 6-, or 7-membered ring. The nitrogen on the 7-membered ring can also be at positions 3, 4, or 6.

Compounds of the invention having the general formula VII:

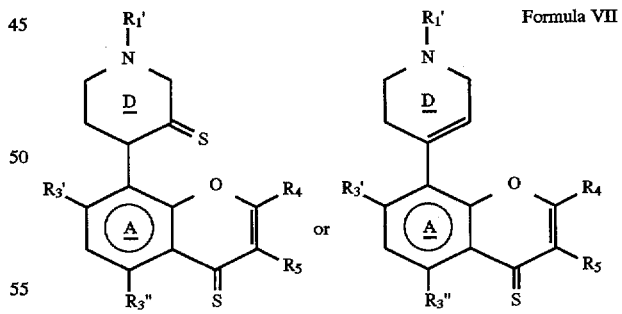

Formula VII which correspond to compounds having a general Formula I, wherein $Z_1$ and $Z_2$ are sulfur can be obtained from the corresponding compound wherein $Z_1$ and $Z_2$ are oxygen (compounds which are obtained for example as depicted in FIG. 1) by methods known in the art. A preferred method for substituting the oxygen of a carbonyl group with a sulfur consists of reacting the compound having a carbonyl group with Lawesson's reagent [2,4-bis(4-methoxyphenyl)-1,3-dithia-2,4-diphosphetane-2,4-disulfide] or $P_2S_5$.

Compounds of general Formula I, wherein $Z_2$ is N can be prepared according to the synthesis scheme represented in FIG. 1, using in place of compound 12, a compound of the general formula:

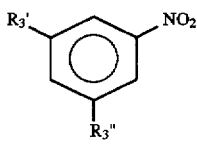

Alternatively, the synthesis can be performed with analogs of the above represented nitrobenzene, wherein the nitro group is replaced by a secondary or tertiary amine. When using such nitrobenzene derived compounds, or analogs thereof, for the synthesis, it may be necessary to protect the oxygen group on the D ring and/or the nitrogen on the A ring. Protection of specific groups can be performed according to methods well known in the art (see for example, "Protective Groups in Organic Synthesis" Theodora W. Greene and Peter G. M. Wuts, Wiley Interscience, John Wiley & Sons, Inc. 1991)

In other embodiments, the subject CDK inhibitors are synthesized by the Stille reaction using as reagents a cyclic compound comprising ring D and a derivative of a chromone comprising ring A. Accordingly, subject CDK inhibitors are synthesized as follows:

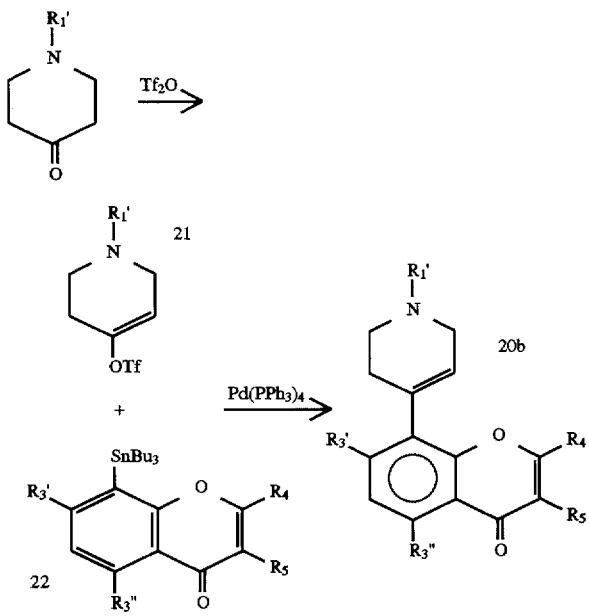

As described above, the OTf group of reagent 21 can be substituted with Br or I. Furthermore, the SnBu$_3$ group of reagent 22 can be substituted with B(OH)$_2$ such that the reaction is a Suzuki reaction. Compound 20b can further be modified to another CDK inhibitor of the invention, by substituting one of the C=C in ring D with a carbonyl group, as described above and in the examples. Such a compound has for example the structure of compound 20a.

Substitutions of the nitrogen atom in ring D can be obtained by methods known in the art and further disclosed in U.S. Pat. No. 4,900,727. Additional reactions that can be used for preparing subject CDK inhibitors are disclosed in the following publications: U.S. Pat. No. 4,179,447 by Connor, D. T. et al.; U.S. Pat. No. 4,841,078 by Eggler, J. F. et al.; U.S. Pat. No. 5,284,856 by Naik, R. G. et al.; U.S. Pat. No. 3,947,462 by Arendsen, D. L. et al.; U.S. Pat. No. 4,853,400 by Parsons, J. H. et al.; U.S. Pat. No. 4,678,787 by Jaen, J. C. et al.; U.S. Pat. No. 4,169,097 by Wright, G. C. et al.; U.S. Pat. No. 5,292,751 by Naik, R. G. et al.; U.S. Pat. No. 4,055,654 by Cairns H. et al.; U.S. Pat. No. 4,814,346 by Albert, A. I. et al.; U.S. Pat. No. 5,196,448 by Ely, P. H. et al.; U.S. Pat. No. 5,416,098 by Labroo, V. M. et al.; and U.S. Pat. No. 4,888,356 by Miyano, M. et al.

Furthermore, Applicants note that a variety of techniques are available in the art for generating combinatorial libraries of small organic molecules such as the subject benzopyran derivatives. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of 1000 to 100,000 or more diversomers of the subject compounds can be synthesized, and, by use of a high throughput assay for detecting CDK inhibitors, such as described below or in PCT publication WO 94/09135, rapidly screened for biological activity. For a review of methods of combinatorial synthesis, and methods of library screening and deconvolution, see, e.g., E. M. Gordon et al. (1994) J. Med. Chem. 37:1385–1401, and references cited therein.

In an exemplary embodiment, a library of substituted 8-piperidyl benzopyran-4-one diversomers can be synthesized according to the techniques described herein and the Still et al. PCT publication WO 94/08051, being linked to a polymer bead by a hydrolyzable or photolyzable group at the 5 or 7 position of the benzopyranone. According to the Still et al. technique, the library is synthesized on a set of beads, each bead including a set of tags identifying the particular diversomer on that bead. The beads can be dispersed on the surface of permeable membrane, and the diversomers released from the beads by lysis of the bead linker. The diversomer from each bead will diffuse across the membrane to an assay zone, where it will interact with a CDK assay. For instance, the CDK4 substrate Rb can be immobilized on the membrane, and phosphorylation of Rb by CDK4 detected by autoradiography using radiolabeled ATP. A diversomer from the library which is capable of inhibiting CDK4 phosphorylation of Rb will be scored for by a zone around its bead which lacks $P^{32}$ labeling of Rb. Such beads can be picked, with the size of the labeling exclusion zone optionally being used to semi-quantatively rank activity, and the encoding tags on the bead used to identify the particular diversomer(s) of interest (e.g., see Still et al., supra).

Figure 2A:
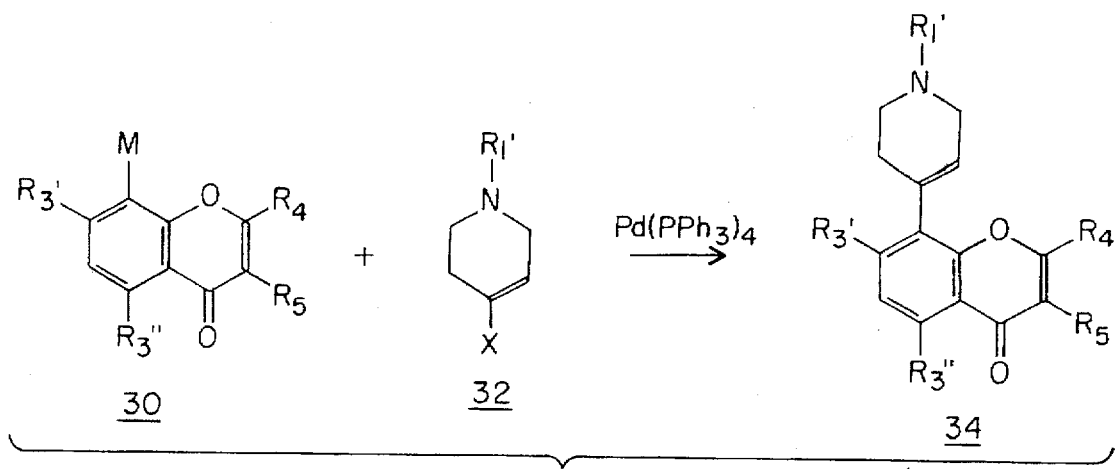
FIGS. 2A and 2B depict general schemes suitable for combinatorial synthesis of compounds of the invention.
Figure 2B:
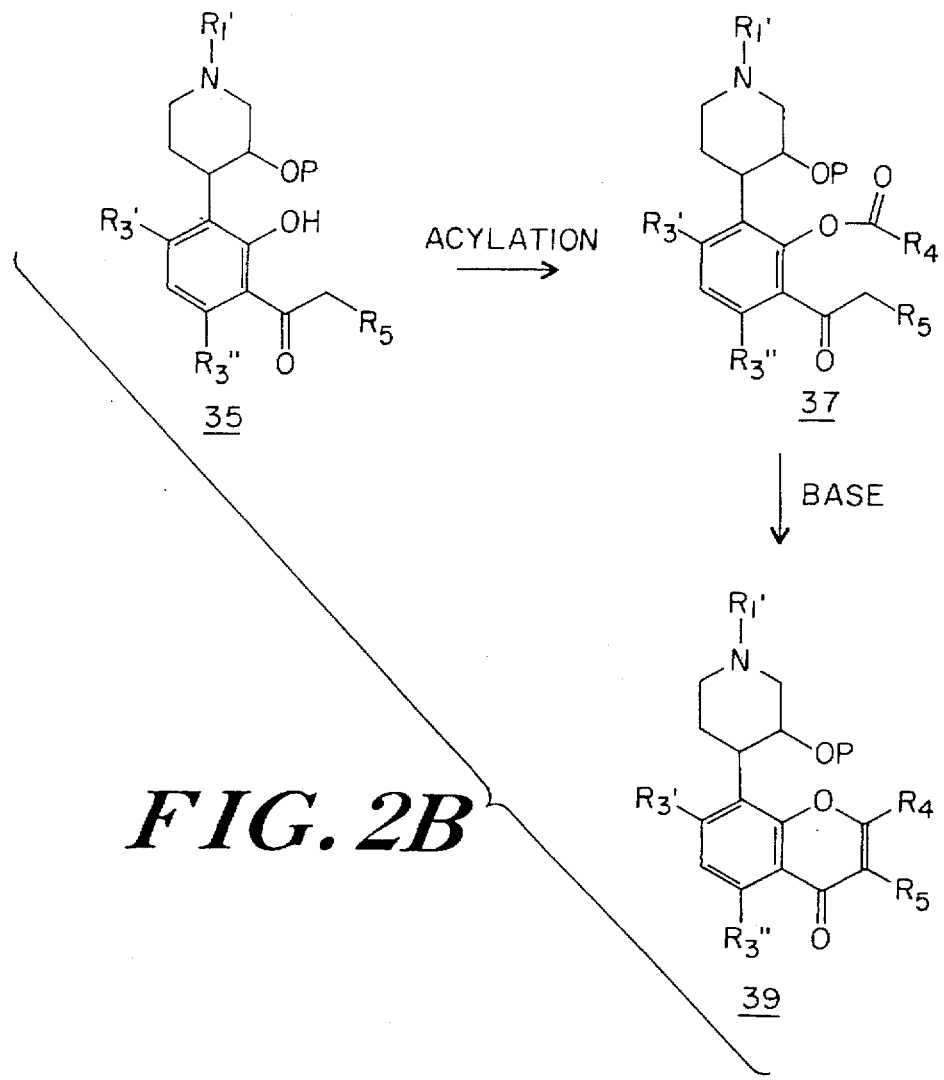

Exemplary reaction schemes suitable for combinatorial synthesis are depicted in FIGS. 2A and 2B. In FIG. 2A, a fragment coupling reaction is used to join two subunits 30 and 32. Thus, for example, M in structure 30 can represent tributyltin or a boronate, while X of compound 32 represents a group such as a halide or triflate. Accordingly, a plurality of different compounds having the general structure 30 (differing, e.g., at $R_3'$, $R_3''$, $R_4$, or $R_5$) can be reacted, under appropriate conditions, with a plurality of different compounds having the general structure 32 (differing, e.g., at $R_1'$) to provide a plurality of different compounds 34. In this scheme, the plurality of compounds 30 or 32 can be immobilized to discrete solid supports, or in arrays on a solid surface, so that the compounds 34 formed by reaction can be individually accessed. Thus, for example, a plurality of aliquots of polymeric beads can each be derivatized with a single compound of structure 30, and the aliquots of beads either pooled or separately treated with individual compounds 32 in a plurality of reaction vessels, to provide a plurality of compounds 34 in which each bead contains only one individual compound.

In another combinatorial reaction scheme, shown in FIG. 2B, a plurality of different compounds 35, in which P represents a protecting group (and differing, e.g., at $R_1'$, $R_3'$, $R_3''$, or $R_5$), can be acylated with a plurality of different acylating agents (providing a plurality of $R_4$ substituents of compound 37), thus providing a diverse collection of different compounds 37, which are cyclized to compounds 39. As described above, the compounds can be synthesized on solid supports for ease of handling and identification.

IV. Exemplary Uses

The invention pertains to novel compounds which are capable of inhibiting cyclin-dependent kinases and are thus capable of regulating cell proliferation. Thus, a preferred use for the compounds of the invention is for inhibiting cell proliferation. In particular, the compounds of the invention can be used for treating a subject having an excessive or abnormal cell growth.

There are a wide variety of pathological cell proliferative conditions for which the compounds of the present invention can provide therapeutic benefits, with the general strategy being the inhibition of an anomalous cell proliferation. To illustrate, cell types which exhibit pathological or abnormal growth include various cancers and leukemias, psoriasis, bone diseases, fibroproliferative disorders such as involving connective tissues, atherosclerosis and other smooth muscle proliferative disorders, as well as chronic inflammation.

In addition to proliferative disorders, the treatment of differentiative disorders which result from, for example, de-differentiation of tissue which may (optionally) be accompanied by abortive reentry into mitosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In addition to therapeutic applications (e.g., for both human and veterinary uses) it will be apparent the subject compounds can be used as a cell culture additive for controlling proliferative and/or differentiation states of cells in vitro, for instance, by controlling the level of activation of a CDK. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. By preventing the activation of a $G_0/G_1$ CDK, the subject inhibitors can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the CDK4 inhibitors can be used for ex vivo tissue generation, as for example, to enhance the generation of prosthetic tissue devices for implantation.

It is likely that inhibition by the compounds of the invention of the catalytic activity of cyclin-dependent kinases is mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated, hyperactive, form of the kinase and situations in which the kinase is present at excessive levels. Such compounds can also block excessive kinase activity in situations in which the cyclin regulating the kinase is present at excessive levels or its binding to the kinase is enhanced. Furthermore, compounds which block kinase activity by interacting with the ATP binding site of the enzyme are also useful for inhibiting kinase activity in situations in which a natural inhibitor of cyclin-kinase complexes is mutated.

It will also be apparent that differential screening assays can be used to select for those compounds of the present invention with specificity for non-human CDK enzymes. Thus, compounds which act specifically on eukaryotic pathogens, e.g., are anti-fungal or anti-parasitic agents, can be selected from the subject benzopyranone inhibitors. To illustrate, inhibitors of the Candida CDK kinase, CKS 1, can be used in the treatment of candidiasis- an opportunistic infection that commonly occurs in debilitated and immunosuppressed patients. CKS1 inhibitors could be used to treat these infections in patients with leukemias and lymphomas, in people who are receiving immunosuppressive therapy, and in patients with such predisposing factors as diabetes mellitus or AIDS, where fungal infections are a particular problem.

By way of illustration, the assays described in the art can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, an assay as described above or in the appended examples can comprise comparing the relative effectiveness of a test compound on inhibiting a mammalian CDK enzyme with its effectiveness towards a CDK enzyme from yeast, such as selected from the group consisting of *Candida albicans, Candida stellatoidea, Candida tropicalis, Candida parapsilosis, Candida krusei, Candida pseudotropicalis, Candida quillermondii,* or *Candida rugosa.* Candida CDK genes have been described, such as in U.S. Ser. No. 08/463,090.

Likewise, the differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans,* or *Aspergillus terreus.*

Likewise, where the mycotic infection is mucormycosis, the CDK assay can be derived from yeast such as *Rhizopus arrhizus, Rhizopus oryzae, Absidia corymbifera, Absidia ramosa,* or *Mucor pusillus.* Sources of other CDK enzymes includes the pathogen *Pneumocystis carinii.*

In addition to such therapeutic uses, anti-fungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms.

In similar fashion, side by side comparison of inhibition of a mammalian CDK and an insect CDK, such as the Drosophilia CDK5 gene (Hellmich et al. (1994) *FEBS Lett* 356:317–21), will permit selection amongst the subject benzopyranone derivatives of inhibitors which discriminate between the human/mammalian and insect enzymes. Accordingly, the present invention expressly contemplates the use and formulations of the subject benzopyranone in insecticides, such as for use in management of insects like the fruit fly.

In yet another embodiment, certain of the subject CDK inhibitors can be selected on the basis of inhibitory specificity for plant CDK's relative to the mammalian enzyme. For example, a plant CDK can be disposed in a differential screen with one or more of the human enzymes to select those benzopyranone compounds of greatest selectivity for inhibiting the plant enzyme. Thus, the present invention specifically contemplates formulations of the subject CDK inhibitors for agricultural applications, such as in the form of a defoliant or the like.

IV. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by inhibiting an intracellular signalling pathway in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present cyclin-dependent inhibitors may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia, or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These peptides and compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The invention now being generally described, it will be more readily understood by reference to the following examples which are included merely for purposes of illustration of certain aspects and embodiments of the present invention, and are not intended to limit the invention.

EXAMPLES

Example 1

Compound 2

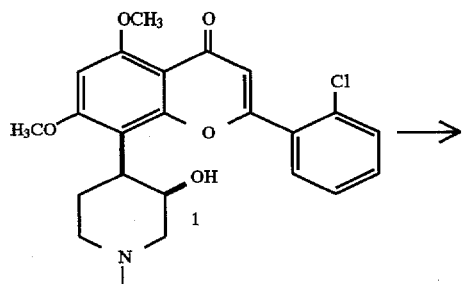

-continued
Compound 2

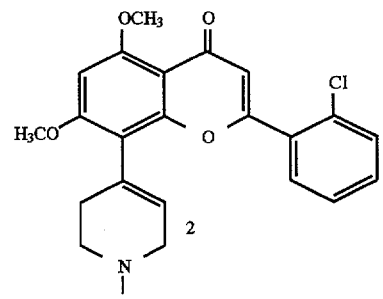

A solution of 5,7-dimethoxy flavopiridol 1 (100 mg, 0.23 mmol) in $CHCl_3$ (1 mL) was cooled to $-50°$ C. Diethyaminosulfurtrifluoride (0.05 mL, 0.35 mmol) was added to the solution and the reaction mixture was allowed to warm to room temperature and stirred for 15 min. The reaction mixture was diluted with $CHCl_3$ and poured into saturated sodium bicarbonate solution. The aqueous layer was extracted with chloroform. The organic extracts were dried and concentrated. The crude product was purified by silica gel chromatography using 2% MeOH/97% $CHCl_3$/1% $NH_4OH$ as the eluant to give the dimethoxy olefin 2 as a foamy solid (31 mg, 33%).

$^1$H NMR ($CDCl_3$, 300 MHz): d 7.3–7.6 (m, 4H); 6.58 (s, 1H); 6.43 (s, 1H); 5.6 (br t, 1H); 4.02(s, 3H); 3.91 (s, 3H); 3.09 (d, J=3 Hz, 2H); 2.64 (t, 2H); 2.39 (br s, 5H).

Example 2

Compound 3

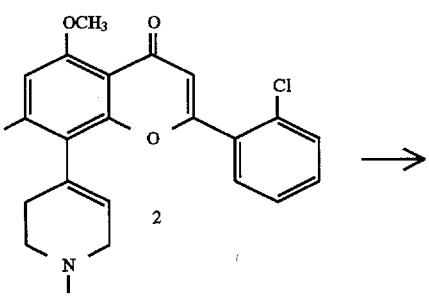

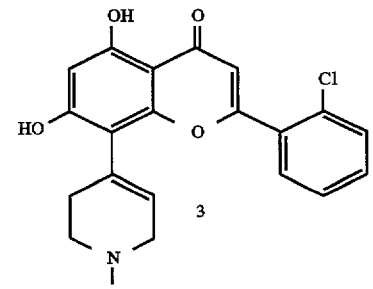

A mixture of dimethoxy olefin 2 (13 mg, 0.03 mmol) and pyridine hydrochloride (120 mg) was heated in a sealed tube to 180° C. for one hour. The reaction was cooled to room temperature. The solid residue was dissolved in saturated sodium bicarbonate solution. The aqueous layer was extracted with 10% MeOH/$CHCl_3$. The organic extracts were dried and concentrated. The crude product was purified by silica gel chromatography using 10% MeOH/89% CHCl₃/1% NH₄OH as eluant to give the olefin 3 (2.4 mg, 21%) as a white solid.

¹H NMR (CDCl₃, 300 MHz): d 7.35–7.6 (m, 4H); 6.52 (s, 1H); 6.34 (s, 1H); 5.8 (br t, 1H); 3.15 (d, 2H); 2.71 (t, 2H); 2.5 (m, 2H); 2.47 (s, 3H).

Example 3

Compound 4

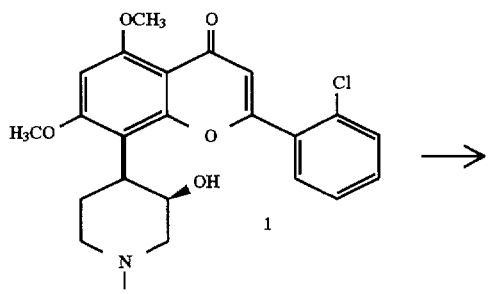

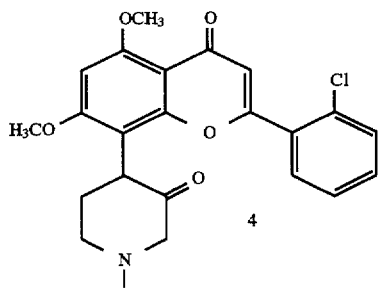

A solution of oxalyl chloride (0.15 mL, 1.75 mmol) in CH₂Cl₂ (2 mL) was cooled to –78° C. A solution of dimethyl sulfoxide (0.26 mL, 3.6 mmol) in CH₂Cl₂ (0.5 mL) was added to the reaction mixture at –78° C. and the reaction mixture was stirred at –78° C. for 15 min. A solution of 5,7 dimethoxy flavopiridol 1 (140 mg, 0.327 mmol) in CH₂Cl₂ (1 mL) was added to the reaction mixture and the stirred for 15 min at –78° C. Triethylamine (1.2 mL, 9 mmol) was added to the reaction mixture and the reaction mixture was allowed to warm to room temperature. The reaction mixture was poured into saturated sodium bicarbonate solution. The aqueous layer was extracted with CHCl₃. The organic extracts were dried and concentrated. The crude product was purified by silica gel chromatography using 4% MeOH/95% CHCl₃/1% NH₄OH as eluant to give the ketone 4 as a viscous oil (89 mg, 64%).

¹H NMR (CDCl₃, 300 MHz): d 7.3–7.65 (m, 4H); 6.49 (s, 1H); 6.46 (s, 1H); 4.1 (dd, 1H), 4.00 (s, 3H); 3.92 (s, 3H); 3.35 (d, J=15.9 Hz, 1H); 2.95 (d, 1H); 2.81 (d, J=15.9 Hz, 1H); 2.34–2.55 (m, 2H); 2.35 (s, 3H); 2.0 (m, 1H).

Example 4

Compound 5

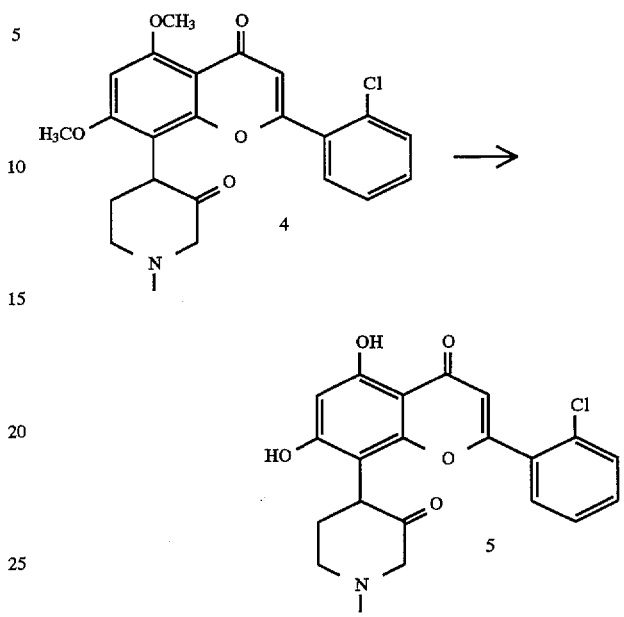

A mixture of dimethoxy ketone 4 (12 mg, 0.028 mmol) and pyridine hydrochloride (120 mg) was heated in a sealed tube at 180° C. for one hour. The reaction was cooled to room temperature. The solid residue was dissolved in saturated sodium bicarbonate solution. The aqueous layer was extracted with 10% MeOH/CHCl₃. The organic extracts were dried and concentrated The crude product was purified by silica gel chromatography using 10% MeOH/89% CHCl₃/1% NH₄OH as eluant to give the ketone 5 (7.4 mg, 66%) as a yellowish solid.

¹H NMR (CDCl₃, 300 MHz): d 12.4 (s, 1H); 7.35–7.6 (m, 4H); 6.46 (s, 1H); 6.35 (s, 1H); 3.5 (br, 1H); 3.2 (d, 1H); 2.6–2.8 (br m, 2H); 2.41 (s, 3H); 2.2–2.4 (br m, 2H); 1.9 (br m, 1H).

Example 5

Compound 6

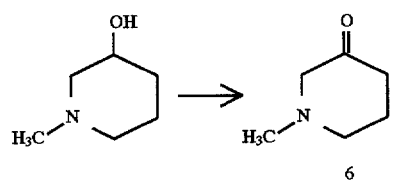

A solution of oxalyl chloride (16.5 mL, 190 mmol) in CH₂Cl₂ (400 mL) was cooled to –78° C. A solution of dimethyl sulfoxide (27 mL, 380 mmol) in CH₂Cl₂ (50 mL) was added to the reaction mixture at –78° C. and the reaction mixture was stirred at –78° C. for 15 min. A solution of 1-methyl-3-piperidinol (20 g, 175 mmol) in CH₂Cl2 (70 mL) was added to the reaction mixture and the stirred for 15 min at –78° C. Triethylamine (106 mL, 760 mmol) was added to the reaction mixture and the reaction mixture was allowed to warm to room temperature. The reaction mixture was poured into saturated sodium bicarbonate solution. The aqueous layer was extracted with CHCl₃. The organic extracts were dried and concentrated. The crude product 6 (16.6 g) was used immediately in the next reaction without further purification.

¹H NMR (CDCl₃, 300 MHz): d2.96 (s, 2H); 2.61 (t, 2H); 2.35 (s, 3H); 2.32 (t, 2H); 1.94 (m, 2H)

Example 6

Compound 7

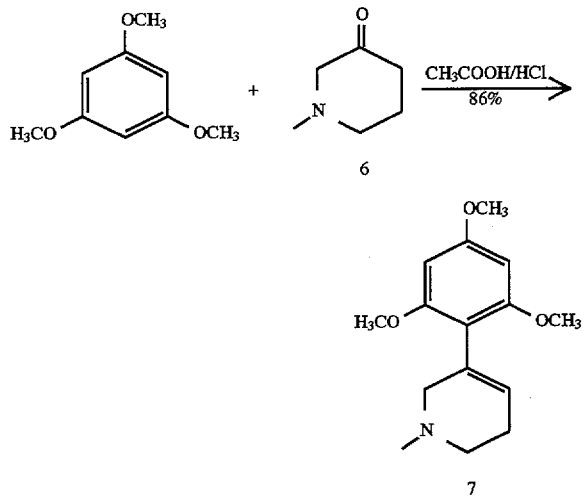

HCl gas was bubbled through a solution of crude, 1-methyl-3-piperidinone 6 (16.6 g, 148 mmol) and tri-methoxybenzene (24.7 g, 148 mmol) in acetic acid (200 mL) for one hour. The reaction mixture was heated to 90° C. and stirred for 3 h. The reaction mixture was cooled to room temperature and the acetic acid was removed under reduced pressure. The residue was dissolved in water and basified with 20% NaOH solution. The aqueous layer was extracted with CHCl₃. The organic extracts were dried and concentrated. The crude product was purified by silica gel chromatography using a MeOH/CHCl₃ gradient as eluant to give the olefin 7 (17.2 g).

¹H NMR (CDCl₃, 300 MHz): d 6.11 (s, 2H); 5.65 (br t, 1H); 3.81 (s, 3H); 3.75 (s, 6H); 3.38 (d, J=1.5 Hz, 2H); 3.02 (t, 2H); 2.65 (s, 3H); 2.45 (m, 2H).

Example 7

Compound 8

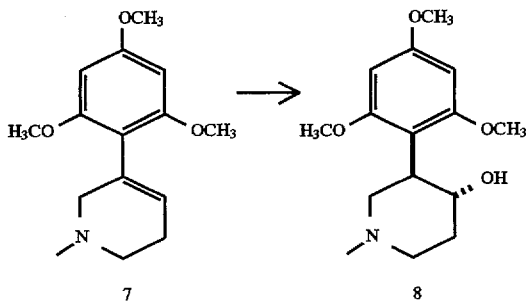

To a solution of olefin 7 (12 g, 46 mmol) and sodium borohydride (6 g, 158 mmol) in THF (150 mL) was added BF₃.OEt₂ (24 mL, 194 mmol). The reaction mixture was warmed to 50° C. and stirred for one hour. The reaction mixture was cooled to 0° C. Water (15 mL), followed by concentrated HCl (60 mL) was added dropwise to the reaction mixture. The reaction mixture was warmed to 60° C. and stirred for 3 hours. The reaction mixture was cooled to 0° C. 40% NaOH solution (120 mL) followed by 30% H₂O₂ (90 mL) was added to the reaction mixture. The reaction mixture was poured into saturated sodium bicarbonate solution. The aqueous layer was extracted with CHCl₃. The organic extracts were dried and concentrated to give crude product. The crude product was dissolved in 2N HCl (300 mL) solution and extracted with ethyl acetate. The aqueous solution was basified with 20% NaOH solution. The aqueous layer was extracted with CHCl₃. The organic extracts were dried and concentrated to give the trans alcohol 8 (5.17 g, 41%).

1H NMR (CDCl₃, 300 MHz): d 6.11 (s, 2H); 4.25 (dt, 1H); 3.8 (s, 3H); 3.75 (s, 6H); 3.5 (dt, 1H); 2.9 (d, 1H); 2.55 (d, 1H); 2.29 (s, 3H); 1.8-2.15 (m, 3H); 1.7 (m, 1H).

Example 8

Compound 9

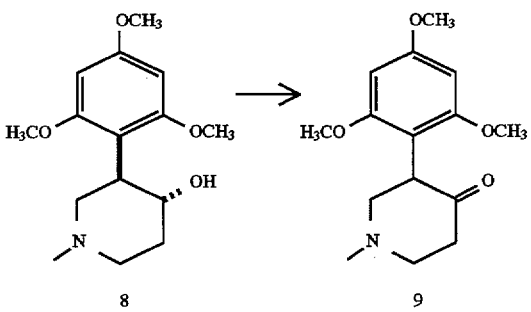

A solution of oxalyl chloride (1.5 mL, 18 mmol) in CH₂Cl₂ (30 mL) was cooled to -78° C. A solution of dimethyl sulfoxide (2.6 mL, 36 mmol) in CH₂Cl₂ (8 mL) was added to the reaction mixture at -78° C. and the reaction mixture was stirred at -78° C. for 15 min. A solution of alcohol 8 (2.5 g, 8.9 mmol) in CH₂Cl₂ (15 mL) was added to the reaction mixture and the stirred for 15 min at -78° C. Triethylamine (10 mL, 72 mmol) was added to the reaction mixture and the reaction mixture was allowed to warm to room temperature. The reaction mixture was poured into saturated sodium bicarbonate solution. The aqueous layer was extracted with CHCl₃. The organic extracts were dried and concentrated. The crude product was purified by silica gel chromatography using 10% MeOH/CHCl₃ - 20% MeOH/CHCl₃ as eluant to give the ketone 9 (1.28 g, 52%).

¹H NMR (CDCl₃, 300 MHz): d 6.13 (s, 2H); 4.2 (dd, 1H); 3.8 (s, 3H); 3.75 (s, 6H); 3.1 (m, 1H); 3.0 (dt, 1H); 2.55 (d, 1H); 2.5-2.75 (m, 4H); 2.4 (s, 3H).

Example 9

Compound 10

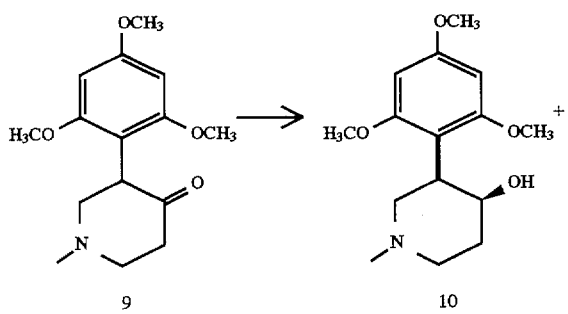

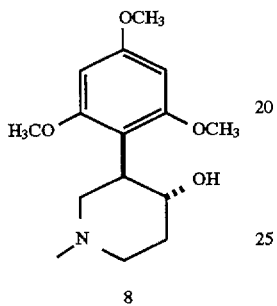

To a refluxing solution of ketone 9 (1.25 g, 4.5 mmol) in ethanol (30 mL) was added sodium borohydride (0.43 g, 11.2 mmol). The reaction mixture was refluxed for one hour, cooled to 0° C. and water was added dropwise to it. The reaction mixture was poured into saturated sodium bicarbonate solution. The aqueous layer was extracted with CHCl$_3$. The organic extracts were dried and concentrated. The crude product was purified by silica gel chromatography using 50% MeOH/CHCl$_3$ - 100% MeOH as eluant to give the cis alcohol 10 (183 mg, 15%) and the trans alcohol 8 (622 mg, 50%).

$^1$H NMR (CDCl$_3$, 300 MHz): d 6.15 (s, 2H); 3.95 (s, 1H); 3.8 (s, 9H); 3.0 (t, 1H); 2.65 (d, 1H); 2.4–2.55 (m, 2H); 2.32 (s, 3H); 2.2 (m, 2H); 1.85 (m, 1H).

Example 10

Compound 11

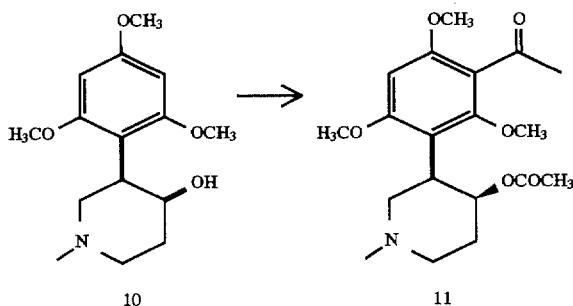

To a solution of cis alcohol 10 (180 mg, 0.64 mmol) in CH$_2$Cl$_2$ (7 mL) was added BF$_3$.OEt$_2$ (0.6 mL, 4.8 mmol), followed by acetic anhydride (0.48 mL, 5 mmol). The reaction mixture was stirred at room temperature for 16 h. The reaction mixture was poured into 10% sodium carbonate solution. The aqueous layer was extracted with CHCl$_3$. The organic extracts were dried and concentrated. The residue obtained was dissolved in CHCl$_3$ and stirred with 10% sodium carbonate solution. The organic layer was separated, dried and concentrated. The crude product was purified by silica gel chromatography using 5% MeOH/CHCl$_3$ as eluant to give the acetophenone 11 (104 mg, 46%).

$^1$H NMR (CDCl$_3$, 300 MHz): d 5.9 (s, 1H); 5.1 (br s, 1H); 3.85 (br s, 3H); 3.8 (br s, 3H); 2.70 (m, 4H); 2.55 (br s, 3H); 2.4 (br s, 5H); 1.95 (br s, 4H).

Example 11

Compound 12

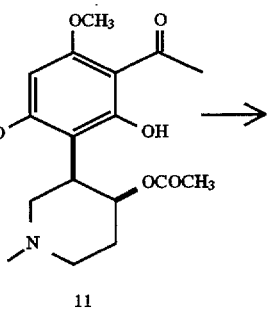

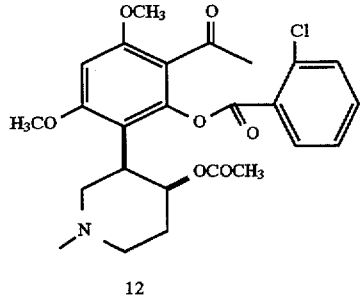

To a solution of phenol 11 (100 mg, 0.28 mmol) in pyridine (4 mL) was added 2-chlorobenzoylchloride (0.12 mL, 0.84 mmol). The reaction mixture was stirred at room temperature for 1 h and poured into saturated sodium bicarbonate solution. The aqueous layer was extracted with CHCl$_3$. The organic extracts were dried and concentrated. The crude product was purified by silica gel chromatography using 2% MeOH/CHCl$_3$ as eluant to give the benzoyl ester 12 (122 mg, 89%).

$^1$H NMR (CDCl$_3$, 300 MHz): d 8.15 (d, 1H); 7.5 (m, 3H); 6.4 (s, 1H); 5.17 (s, 1H); 3.95 (s, 3H); 3.9 (s, 3H); 3.85 (s, 1H); 3.2 (t, 1H); 3.05 (m, 2H); 2.5 (s, 3H); 2.4 (s, 3H); 2.32 (d, 1H); 2.15 (t, 1H); 2.0 (s, 3H); 1.88 (d, 1H).

Example 12

Compound 13

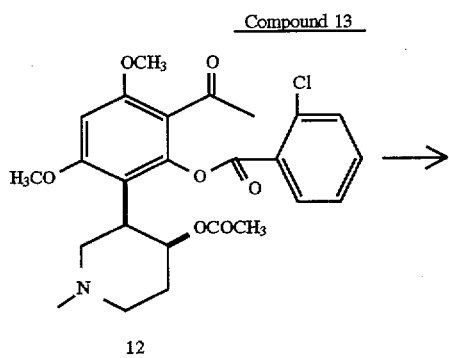

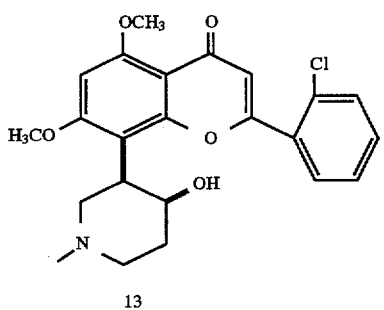

To a solution of benzoyl ester 12 (115 mg, 0.23 mmol) in THF (5 mL) was sodium hydride (50 mg of a 60% suspension, 1.2 mmol). The reaction mixture was stirred at 50° C. for 1.5 h, cooled to 0° C. and a minimum amount of methanol was added dropwise to quench excess NaH. HCl gas was bubbled through the reaction mixture till it was acidic. The reaction mixture was ice cooled and 10% sodium carbonate solution was added to it until the pH was basic. The aqueous layer was extracted with $CHCl_3$. The organic extracts were dried and concentrated. The crude product was purified by silica gel chromatography using 5% MeOH/94% $CHCl_3$/1% $NH_4OH$ as eluant to give the dimethoxy flavone 13 (48 mg, 49%).

$^1$H NMR ($CDCl_3$, 300 MHz): d 7.25–7.6 (m, 4H); 6.5 (s, 2H); 4.15 (s, 1H); 4.0 (s, 3H); 3.95 (s, 3H); 3.15 (t, 1H); 2.6 (m, 2H); 2.25–2.5 (m, 2H); 2.3 (s, 3H); 1.9 (m, 2H).

Example 13

Compound 14

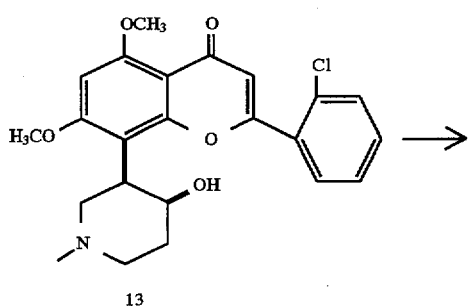

-continued
Compound 14

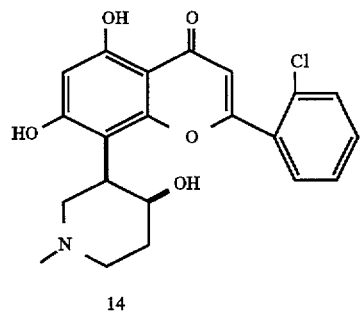

A mixture of dimethoxy flavone 13 (14 mg, 0.03 mmol) and pyridine hydrochloride (150 mg) was heated in a sealed tube at 180° C. for one hour. The reaction was cooled to room temperature. The solid residue was dissolved in saturated sodium bicarbonate solution. The aqueous layer was extracted with 10% MeOH/$CHCl_3$. The organic extracts were dried and concentrated. The crude product was purified by silica gel chromatography using 20% MeOH/79% $CHCl_3$/1% $NH_4OH$ as eluant to give the dihydroxy flavone 14 (5.7 mg, 47%).

$^1$H NMR ($CDCl_3$, 300 MHz): d 12.35 (s, 1H); 7.75 (d, 1H); 7.35–7.55 (m, 3H); 6.5 (s, 1H); 6.35 (s, 1H); 4.1 (s, 1H); 3.95 (m, 1H); 3.1 (m, 3H); 2.7 (dd, 1H); 2.45 (s, 3H); 1.9 (m, 2H).

Example 14

Inhibition of Cdk4/Cyclin D Kinase Activity

This example is an illustration of the cyclin-dependent kinase inhibitory activity of the compounds of the invention. The kinase inhibitory activity of several compounds of the invention was determined using an in vitro kinase assay in which the kinase activity of the CDK4 kinase was measured using a Cyclin D1/cdk4 phosphoRb Assay. Briefly, the assay employs cell lysates from insect cells expressing cyclin D1 and cdk4 kinase. The cyclin/cdk lysate is combined in a microtitre-type plate along with a kinase compatible buffer, $^{32}$P-labeled ATP, a GST-Rb fusion protein, and the test agent. The kinase reaction is allowed to proceed with the radiolabeled ATP, then effectively stopped by the addition of a large excess of unlabeled ATP. The GST-Rb protein is sequestered on a GSH-Sepharose bead suspension, washed, resuspended in scintilant, and $^{32}$P activity detected in a scintillation counter. The concentration of compound at which 50% of the kinase activity was blocked ($IC_{50}$) was calculated for each compound. The results are indicated in Table I.

TABLE I

Inhibition of CDK4/Cyclin D1

| MTX | Structure | Formula | MW | IC$_{50}$(μM) |
|---|---|---|---|---|
| Compound 4 | 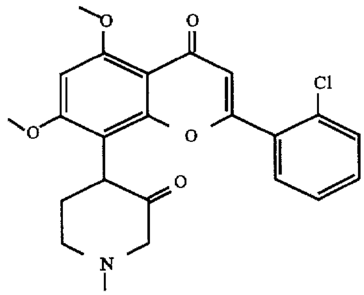 | C$_{23}$H$_{22}$ClNO$_5$ | 427.8885 | 230 |
| Compound 5 | 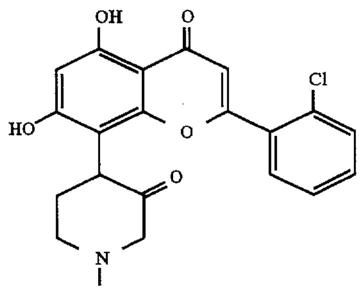 | C$_{21}$H$_{18}$ClNO$_5$ | 399.8343 | <50 |
| Compound 1 | 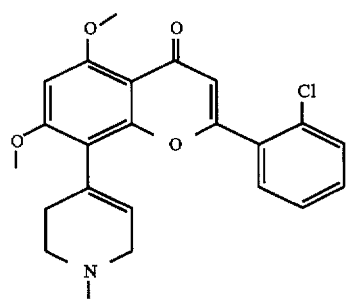 | C$_{23}$H$_{22}$ClNO$_4$ | 411.8891 | <250 |
| Compound 3 | 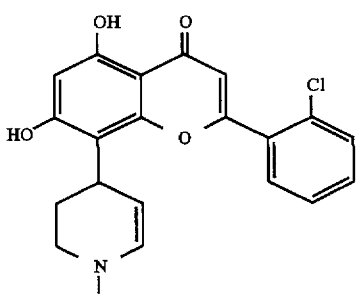 | C$_{21}$H$_{18}$ClNO$_4$ | 383.8349 | <50 |
| Compound 13 | 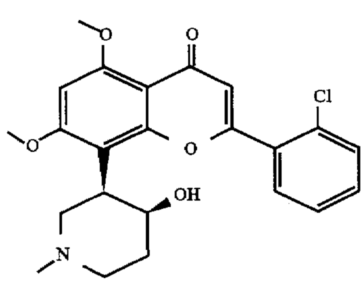 | C$_{23}$H$_{24}$ClNO$_5$ | 429.9044 | <250 |

TABLE I-continued

Inhibition of CDK4/Cyclin D1

| MTX | Structure | Formula | MW | IC$_{50}$(μM) |
|---|---|---|---|---|
| Compound 14 | (see structure) | $C_{21}H_{20}ClNO_5$ | 401.8503 | <150 |

The results indicate that the compounds are able to inhibit 50% of the activity of CDK4/cyclin D1 at a concentration of 250 μM or less. Moreover, the results indicated that compounds in which the groups attached to the aromatic ring of the chromone are hydroxyls (compounds Compound 5 and Compound 3) are much more potent inhibitors of CDK4/cyclin D1 than compounds in which the groups attached to the aromatic ring of the chromone are esters or ethers (compounds Compound 4 and Compounds 1).

Example 15

Inhibition of Cell Proliferation with Chromone Derivatives

To test the activity of certain of the compounds tested in Example 14, we provided test compounds in cell cultures and detected the effect of these drugs on cell-cycle progression by the colorimetric cytotoxicity test using sulforhodamine B (see Skehan et al. (1990) *J Natl Cancer Inst* 82:1107–12). Briefly, BT549, MB453, MCF7 and MG63 are cultured in the presence of various concentrations of test compounds. At different time points, cells in selected test plates are fixed with trichloroacetic acid and stained with sulforhodamine B (SRB). Unbound dye was removed by washing, and protein-bound dye was extracted for determination of optical density.

Following this protocol, the two compounds designated in Example 14 as Compound 5 and Compound 3 showed the following spectrum of inhibitory activity.

| MTX | BT549 (Breast) | MB453 (Breast) | MCF7 (Breast) | MG63 (Bone) |
|---|---|---|---|---|
| Compound 5 | ++ | ++ | ++ | + |
| Compound 3 | ++++ | ++++ | ++++ | +++ |

+ = antiproliferative at 25 μg/ml
++ = antiproliferative at 25 μg/ml, 5 μg/ml
+++ = antiproliferative at 25 μg/ml, 5 μg/ml, 1 μg/ml
++++ = antiproliferative at 25 μg/ml, 5 μg/ml, 1 μg/ml, 0.2 μg/ml All of the above-cited references and publications are hereby incorporated by reference.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:

1. A compound represented by the general formula:

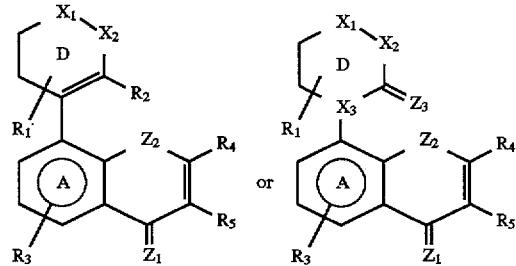

wherein, $Z_1$ and $Z_3$ each can independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

$R_1$ and $R_3$ represents one or more substitutions to the $\underline{D}$ ring and the benzene $\underline{A}$ ring, respectively; and $R_1$, $R_2$, $R_3$, $R_4$, and $R_5$ each independently represent hydrogen, a halogen, a lower alkyl, a lower alkenyl, a lower alkynyl, a carbonyl, a thiocarbonyl, an amine, amide, a cyano, a nitro, an azido, a sulfate, a sulfonate, a sulfonamide, —(CH$_2$)$_m$—R$_8$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_8$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_8$, R$_8$ represents a substituted or unsubstituted aryl, an aralkyl, a cycloalkyl, a cycloalkenyl, or a heterocycle; and n and m are independently for each occurrence zero or an integer in the range of 1 to 6.

2. The compound of claim 1, wherein each occurrence of R$_3$ independently represent a hydroxyl, a hydroxyl-substituted lower alkyl, an alkoxyl, —O—C(O)—R'$_{12}$ or an —O—C(O)—R'$_{12}$ substituted lower alkyl, wherein, R'$_{12}$ represent R'$_{12}$ represents a hydrogen, an alkyl, an alkenyl or —(CH$_2$)$_m$—R$_8$, R$_8$ represents a substituted or unsubstituted aryl, an aralkyl, a cycloalkyl, a cycloalkenyl, or a heterocycle; and n and m are independently for each occurrence zero or an integer in the range of 1 to 6.

3. The compound of claim 2, wherein $R_3$ represents a hydroxyl group.

4. The compound of claim 3, wherein $Z_1$, $Z_2$, and $Z_3$ represent O.

5. The compound of claim 4, wherein $X_1$ represents N and $X_2$ represents C.

6. The compound of claim 5, wherein $R_4$ is $-(CH_2)_m-R_8$, m is 0, and $R_8$ represents a substituted or unsubstituted ring selected from a group consisting of benzene, pyrrole, furan, thiophene, imidazole, oxazole, thiazole, triazole, pyrazole, pyridine, pyrazine, pyridazine and pyrimidine.

7. The compound of claim 6, which is an inhibitor of cyclin-dependent kinases.

8. The compound of claim 7, wherein the cyclin-dependent kinases are active in $G_0$ or early $G_1$ stage of the cell cycle.

9. The compound of claim 7, which compound is an inhibitor of a mammalian cyclin dependent kinase.

10. The compound of claim 7, which compound is an inhibitor of an insect cyclin dependent kinase.

11. The compound of claim 7, which compound is an inhibitor of a fungal cyclin dependent kinase.

12. The compound of claim 11, wherein the fungal cyclin dependent kinase is a CDK of a human pathogen selected from a group consisting of *Candida albicans, Candida stellatoidea, Candida tropicalis, Candida parapsilosis, Candida krusei, Candida pseudotropicalis, Candida quillermondii, Candida rugosa, Aspergillus fumigatus, Aspergillus flavus, Aspergillus niger, Aspergillus nidulans, Aspergillus terreus, Rhizopus arrhizus, Rhizopus oryzae, Absidia corymbifera, Absidia ramosa,* and *Mucor pusillus.*

13. A compound represented by the general formula:

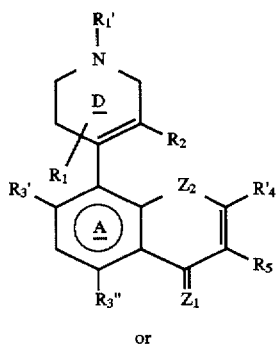

or

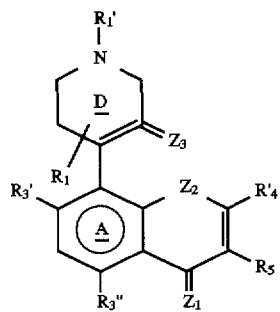

$Z_1$ and $Z_3$ each independently represent O or S;
$Z_2$ represents N, S or O;
$R'_4$ represents an aromatic ring selected from a group consisting of benzene, pyrrole, furan, thiophene, imidazole, oxazole, thiazole, triazole, pyrazole, pyridine, pyrazine, pyridazine and pyrimidine, the aromatic ring being unsubstituted or alternatively substituted at one or more ring positions with halogens, alkyls, alkenyls, alkynyls, hydroxyl, amino, nitro, thiol amines, imines, amides, phosphonates, phosphines, carbonyls, thiocarbonyls, amides, amine, sulfonyls, ketones, aldehydes, esters, or $-(CH_2)_m-R_8$, $-CF_3$, $-CN$;

$R_1$ and $R_3$ represents one or more substitutions to the $\underline{D}$ ring and the benzene $\underline{A}$ ring, respectively; and $R_1$, $R_2$, $R_3'$, $R_3''$, and $R_5$ each independently represent hydrogen, a halogen, a lower alkyl, a lower alkenyl, a lower alkynyl, a carbonyl, a thiocarbonyl, an amine, amide, a cyano, a nitro, an azido, a sulfate, a sulfonate, a sulfonamide, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, $R_{1'}$ represents hydrogen, an alkyl, an aralkyl, an aryl, a cycloalkyl, $-C(O)$-lower alkyl, $-C(O)$-lower alkenyl, or $-C(O)-(CH_2)_m-R_8$;

$R_8$ represents a substituted or unsubstituted aryl, an aralkyl, a cycloalkyl, a cycloalkenyl, or a heterocycle; and n and m are independently for each occurrence zero or an integer in the range of 1 to 6.

14. The compound of claim 13, wherein the aromatic ring $R'_4$ is a benzene ring which is substituted at one or more ring positions with halogens.

15. The compound of claim 14, wherein $R_3'$ and $R_3''$ each independently represent a hydroxyl, a hydroxyl-substituted lower alkyl, an alkoxyl, an ester, a carboxylate or a salt thereof.

16. The compound of claim 14, wherein $R_3'$ and $R_3''$ represent hydroxyl groups.

17. The compound of claim 16, wherein the active ingredient is an inhibitor of cyclin-dependent kinases.

18. The compound of claim 17, wherein the cyclin-dependent kinases are active in $G_0$ or early $G_1$ stage of the cell cycle.

19. A compound represented by the general formula:

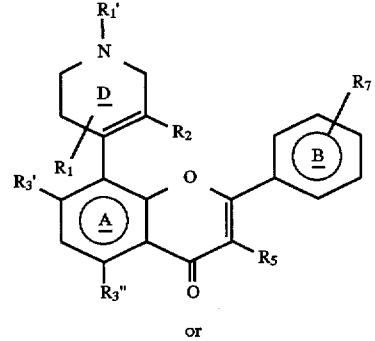

or

-continued

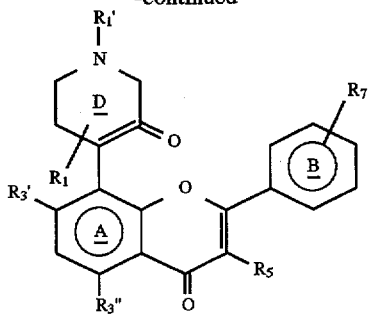

wherein,

R₇ represents one or more substitutions of the benzene ring B;

$R_1$, $R_2$, $R_3'$, $R_3''$, $R_5$, and $R_7$ each independently represent hydrogen, a halogen, $R_{12}$ represents hydrogen, a halogen, a lower alkyl, a lower alkenyl, a lower alkynyl, a carbonyl, a thiocarbonyl, an amine, an amide, a cyano, a nitro, an azido, a sulfate, a sulfonate, a sulfonamide, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$, $R_{1'}$ represents hydrogen, an alkyl, an aralkyl, an aryl, a cycloalkyl, —C(O)-lower alkyl, —C(O)-lower alkenyl, or —C(O)—$(CH_2)_m$—$R_8$;

$R_8$ represents a substituted or unsubstituted aryl, a cycloalkyl, a cycloalkenyl, or a heterocycle; and n and m are independently for each occurrence zero or an integer in the range of 1 to 6.

20. The compound of claim 19, which is an inhibitor of cyclin-dependent kinases.

21. The compound of claim 20, wherein the cyclin-dependent kinases are active in Go or early G1 stage of the cell cycle.

22. The compound of claim 21, wherein $R_2$ and $R_5$ represent hydrogen.

23. The compound of claim 22, wherein $R_7$ represents a halogen.

24. The compound of claim 23, wherein the halogen is chlorine.

25. The compound of claim 24, wherein the chlorine is in an ortho position.

26. The compound of claim 19, wherein $R_3'$ and $R_3''$ each independently represent a hydroxyl, a hydroxyl-substituted lower alkyl, an alkoxyl, an ester, a carboxylate, or a salt thereof.

27. The compound of claim 19, wherein $R_3'$ and $R_3''$ represent hydroxyl.

28. The compound of claim 19, wherein $R_1$ represents hydrogen.

29. A pharmaceutical preparation comprising a pharmaceutically acceptable carrier and a CDK inhibitor in an amount adequate to inhibit proliferation of a eukaryotic cell, which inhibitor is represented in the general formula:

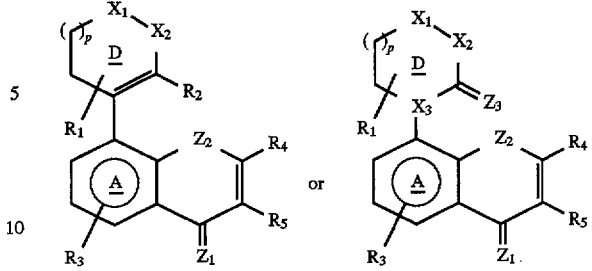

wherein, $Z_1$ and $Z_3$ each can independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

p is 0, 1, or 2;

$R_1$ and $R_3$ represents one or more substitutions to the D ring and the benzene A ring, respectively; and $R_1$, $R_2$, $R_3$, $R_4$, and $R_5$ each independently represent hydrogen, a halogen, a lower alkyl, a lower alkenyl, a lower alkynyl, a carbonyl, a thiocarbonyl, an amine, an amide, a cyano, a nitro, an azido, a sulfate, a sulfonate, a sulfonamide, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$, $R_8$ represents a substituted or unsubstituted aryl, an aralkyl, a cycloalkyl, a cycloalkenyl, or a heterocycle; and n and m are independently for each occurrence zero or an integer in the range of 1 to 6.

30. The pharmaceutical preparation of claim 29, wherein the cell is a mammalian cell.

31. The pharmaceutical preparation of claim 29, wherein the cell is a human pathogen.

32. The pharmaceutical preparation of claim 31, wherein the inhibitor inhibits a cyclin dependent kinase of the human pathogen with an $IC_{50}$ at least order of magnitude less than an $IC_{50}$ for inhibition of a human cyclin dependent kinase.

33. The pharmaceutical preparation of claim 31, wherein the human pathogen selected from a group consisting of *Candida albicans, Candida stellatoidea, Candida tropicalis, Candida parapsilosis, Candida krusei, Candida pseudotropicalis, Candida quillermondii, Candida rugosa, Aspergillus fumigatus, Aspergillus flavus, Aspergillus niger, Aspergillus nidulans, Aspergillus terreus, Rhizopus arrhizus, Rhizopus oryzae, Absidia corymbifera, Absidia ramosa,* and *Mucor pusillus.*

34. The pharmaceutical preparation of claim 29, wherein the cell is an insect cell.

35. The pharmaceutical preparation of claim 34, wherein the inhibitor inhibits a cyclin dependent kinase of an insect with an $IC_{50}$ at least order of magnitude less than an $IC_{50}$ for inhibition of a human cyclin dependent kinase.

36. A method for treating a subject having a disorder associated with excessive cell proliferation, comprising administering to the subject a therapeutically effective amount of the a CDK inhibitor such that the excessive cell proliferation in the subject is reduced, which CDK inhibitor is represented in the general formula

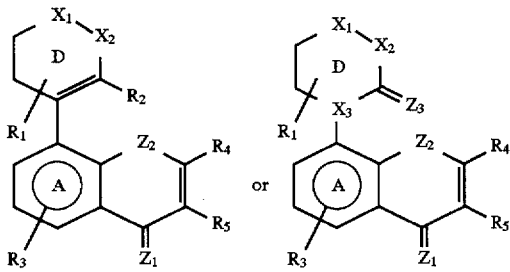

wherein, $Z_1$ and $Z_3$ each independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

$R_1$ and $R_3$ represents one or more substitutions to the $\underline{D}$ ring and the benzene $\underline{A}$ ring, respectively; and $R_1$, $R_2$, $R_3$, $R_4$, and $R_5$ each independently represent hydrogen, a halogen, a lower alkyl, a lower alkenyl, a lower alkynyl, a carbonyl, a thiocarbonyl, an amine, an amide, a cyano, a nitro, an azido, a sulfate, a sulfonate, a sulfonamide, $-(CH_2)_m-R_8$, $-(CH_2)_m-OH$, $-(CH_2)_m-$O-lower alkyl, $-(CH_2)_m-$O-lower alkenyl, $-(CH_2)_n-O-(CH_2)_m-R_8$, $-(CH_2)_m-SH$, $-(CH_2)_m-$S-lower alkyl, $-(CH_2)_m-$S-lower alkenyl, $-(CH_2)_n-S-(CH_2)_m-R_8$, $R_8$ represents a substituted or unsubstituted aryl, a cycloalkyl, a cycloalkenyl, or a heterocycle; and n and m are independently for each occurrence zero or an integer in the range of 1 to 6.

37. A method for treating a subject having a disorder associated with de-differentiation of a differentiated cell population, comprising administering to the subject a therapeutically effective amount of the a CDK inhibitor such that de-differentiation of the cell population in the subject is reduced, which CDK inhibitor is represented in the general formula

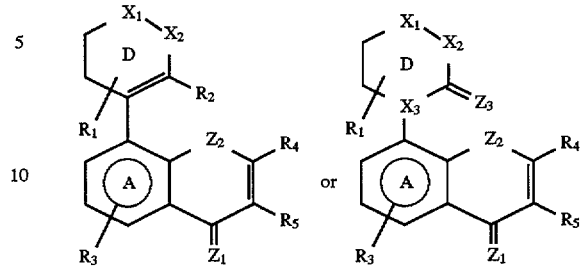

wherein, $Z_1$ and $Z_3$ each can independently represent O or S;

$Z_2$ represents N, S or O;

$X_1$ and $X_2$ each independently represent C or N, with the proviso that if one of $X_1$ or $X_2$ is N, the other is C;

$X_3$ represents C or N;

$R_1$ and $R_3$ represents one or more substitutions to the $\underline{D}$ ring and the benzene $\underline{A}$ ring, respectively; and $R_1$, $R_2$, $R_3$, $R_4$, and $R_5$ each independently represent hydrogen, a halogen, a lower alkyl, a lower alkenyl, a lower alkynyl, a carbonyl, a thiocarbonyl, an amine, an amide, a cyano, a nitro, an azido, a sulfate, a sulfonate, a sulfonamide, $-(CH_2)_m-R_8$, $-(CH_2)_m-OH$, $-(CH_2)_m-$O-lower alkyl, $-(CH_2)_m-$O-lower alkenyl, $-(CH_2)_n-O-(CH_2)_m-R_8$, $-(CH_2)_m-SH$, $-(CH_2)_m-$S-lower alkyl, $-(CH_2)_m-$S-lower alkenyl, $-(CH_2)_n-S-(CH_2)_m-R_8$, $R_8$ represents a substituted or unsubstituted aryl, an aralkyl, a cycloalkyl, a cycloalkenyl, or a heterocycle; and n and m are independently for each occurrence zero or an integer in the range of 1 to 6.

* * * * *